(12) United States Patent
Collin et al.

(10) Patent No.: US 10,233,151 B2
(45) Date of Patent: Mar. 19, 2019

(54) USE OF A NOVEL 3-ARYL-4-CATECHOL-PYRROLE-N-PROPANOL COMPOUND AND THE DERIVATIVES THEREOF TO TREAT CANCER AND DISEASES RELATED TO EXCESSIVE ANGIOGENESIS

(71) Applicant: Centre National de la Recherche Scientifique (CNRS), Paris (FR)

(72) Inventors: Pascal Collin, Buc (FR); Bernard Delpech, Clamart (FR); Joanna Bakala, Paris (FR); Bogdan Iorga, Antony (FR); Yves-Michel Frapart-Jannuad, Ecury sur Coole (FR); Fabienne Peyrot, Ivry (FR); Franck Pelissier, Gif S/Yvette (FR); Maria Conception Achab, Gif S/Yvette (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 15/319,579

(22) PCT Filed: Jun. 17, 2015

(86) PCT No.: PCT/EP2015/063613
§ 371 (c)(1),
(2) Date: Dec. 16, 2016

(87) PCT Pub. No.: WO2015/193382
PCT Pub. Date: Dec. 23, 2015

(65) Prior Publication Data
US 2017/0121283 A1    May 4, 2017

(30) Foreign Application Priority Data
Jun. 17, 2014   (FR) ...................................... 14 55554

(51) Int. Cl.
| | | |
|---|---|---|
| *C07D 403/10* | (2006.01) | |
| *C07D 207/333* | (2006.01) | |
| *C07D 207/325* | (2006.01) | |
| *C07D 405/10* | (2006.01) | |

(52) U.S. Cl.
CPC ..... *C07D 207/333* (2013.01); *C07D 207/325* (2013.01); *C07D 403/10* (2013.01); *C07D 405/10* (2013.01)

(58) Field of Classification Search
CPC .................................................. C07D 403/10
See application file for complete search history.

(56) References Cited

U.S. PATENT DOCUMENTS

2008/0108648 A1   5/2008 Alcouffe et al.

FOREIGN PATENT DOCUMENTS

FR    2996847    4/2014

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wiki/Cancer.*
International Search Report dated Aug. 4, 2015, in corresponding PCT Application No. PCT/EP2015/063613.
Kerbel et al., *Clinical Translation of Angiogenesis Inhibitors*, 2 Nature Reviews Cancer 727-739 (Oct. 2002).

\* cited by examiner

*Primary Examiner* — Shawquia Jackson
(74) *Attorney, Agent, or Firm* — Buchanan Ingersoll & Rooney PC

(57) ABSTRACT

The present invention relates to a 3-aryl-4 catechol-pyrrole-n-propanol compound and the derivatives thereof having General Formula (I), wherein:—$R^1$ is an aryl group, particularly a phenyl, optionally substituted by one or more $(C_1-C_2)$alkyl groups, one or more halogens, one or more —OH, —CN or $CF_3$ groups, or a combination of same, and—$R^2$ is a $(C_1-C_6)$alkyl group, a hydroxy$(C_1-C_6)$alkyl group, a $(C_1-C_4)$alcoxy$(C_1-C_6)$alkyl group, or a pharmaceutically acceptable hydrate or solvate of same. The invention also relates to the methods for preparing said compound and derivatives, to the pharmaceutical compositions containing same, and to the use of same as a drug or in the form of a prodrug converted via dimerization, particularly via oxidative coupling in the presence of a superoxide anion, in the treatment of cancer and diseases related to excessive angiogenesis.

(I)

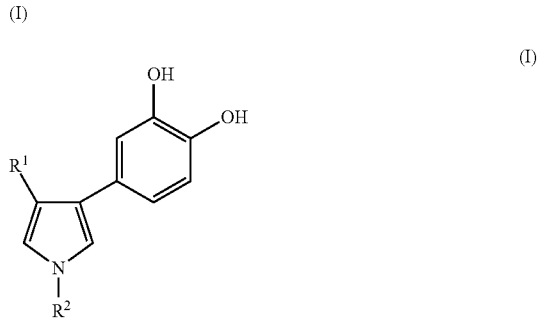

19 Claims, 20 Drawing Sheets

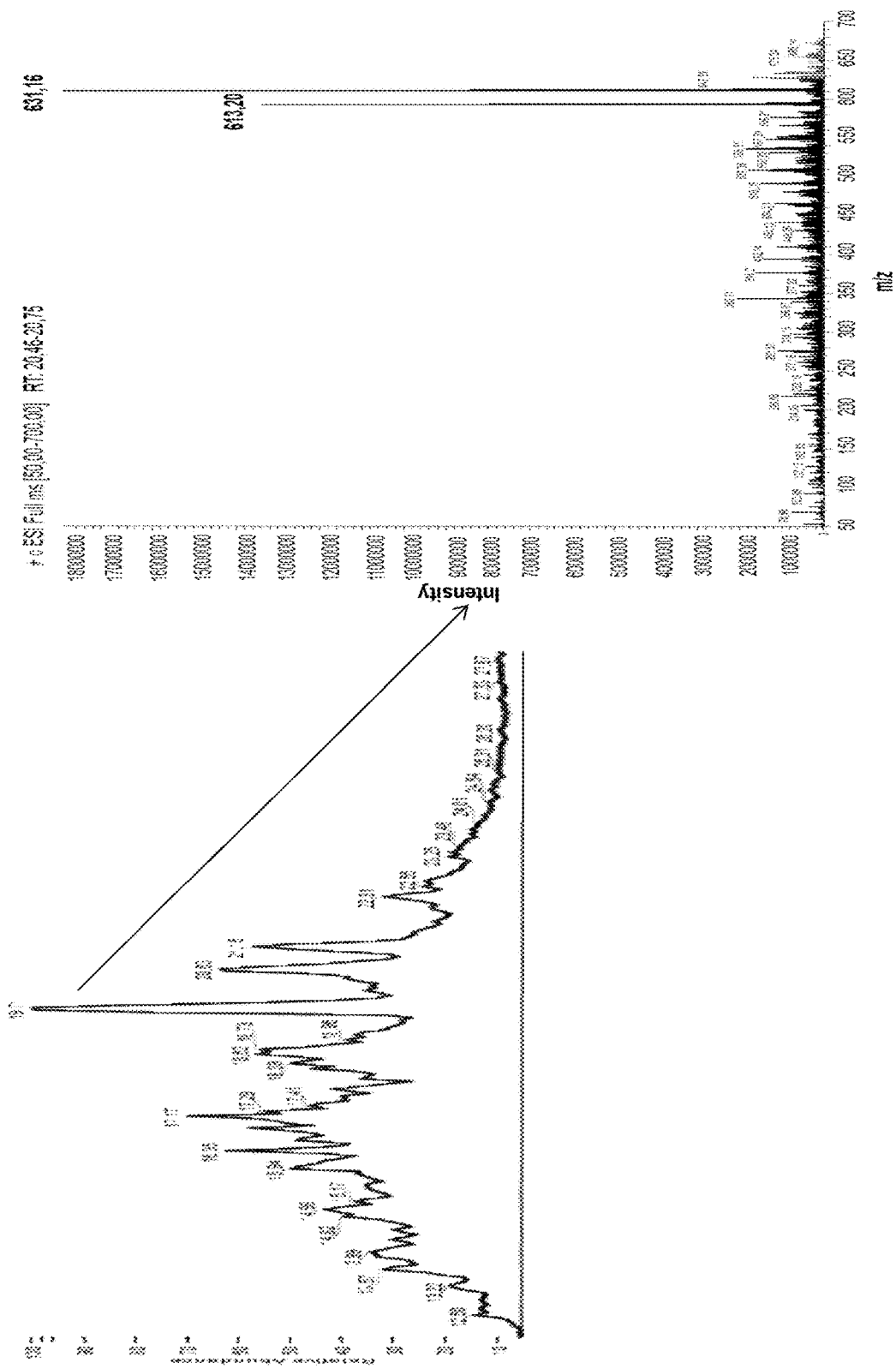
Fig. 4A (continuation)

|  | HCT-116 | | U87 | |
|---|---|---|---|---|
|  | Normoxia | Hypoxia | Normoxia | Hypoxia |
| NT | 235 pg/ml | 602 pg/ml | 1831 pg/ml | 1976 pg/ml |
| 5µM | 190 pg/ml |  |  | 1958 pg/ml |
| 10µM | 228 pg/ml | 626 pg/ml | 1809 pg/ml | 1970 pg/ml |
| 25µM |  | 688 pg/ml | 1866 pg/ml | 2343 pg/ml |
| 50µM | 267 pg/ml | 648 pg/ml | 1869 pg/ml | 2283 pg/ml |

| HCT | 6.5μM |
|---|---|
| U87 | 8μM |
| MDA | 20μM |
| K562 | 6μM |
| K562 R | 12.5μM |
| A549 | 15μM |
| MCF7 | 15μM |

Fig. 7A

USE OF A NOVEL 3-ARYL-4-CATECHOL-PYRROLE-N-PROPANOL COMPOUND AND THE DERIVATIVES THEREOF TO TREAT CANCER AND DISEASES RELATED TO EXCESSIVE ANGIOGENESIS

CROSS-REFERENCE TO RELATED APPLICATIONS

This application is a U.S. National Stage Application pursuant to 35 U.S.C. § 371 of International Patent Application PCT/EP2015/063613, filed on Jun. 17, 2015, and published as WO 2015/193382 on Dec. 23, 2015, which claims priority to French Patent Application 1455554, filed on Jun. 17, 2014, all of which are incorporated herein by reference in their entireties for all purposes.

FIELD OF THE INVENTION

The present invention relates to a novel compound, 3-aryl-4-catechol-N-1H-pyrrole and the derivatives thereof, and to the method for preparing same, the pharmaceutical compositions containing same and the use of same as a drug, particularly to treat cancer and diseases associated with excessive angiogenesis.

PRIOR ART

Tumor development integrates at least three principal biological phenomena:

1. uncontrolled multiplication of tumor cells associated with inhibition of apoptosis and activation of survival and proliferation pathways,
2. abnormal peritumoral angiogenesis,
3. presence of a hypoxic region in the center of the tumor, at a distance from blood vessels, leading to phenotypical changes in the cancer cells, often the origin of mechanisms of chemotherapy resistance.

Current anticancer treatments which target the first phenomenon block the uncontrolled multiplication of cancer cells, either by inhibition of antiapoptotic factors or inhibition of cell division or the survival process. Although these treatments, which are often part of a multitherapeutic approach, provide a real benefit in cancer treatment, they are not sufficient to eradicate all the cancer cells because they target only part of the mechanisms that contribute to tumor growth. To this disadvantage is added the problem of target specificity, compared to normal cells, as well as mechanisms of resistance.

Recent research has established a new therapeutic approach whose objective is inhibition of the peritumoral angiogenesis process. Indeed, angiogenesis is essential to tumor growth in both normoxia and hypoxia. It is promoted by the secretion of vascular endothelial growth factor (VEGF) by tumor cells, and amplified by the hypoxic state due to synthesis of the transcription factor HIFα. Most of the antiangiogenic drugs used correspond either to antibodies directed against VEGF or to compounds directed against the VEGF receptor. Unfortunately, the clinical results of antiangiogenic therapies are very modest and are often associated with mechanisms of resistance and an increased risk of invasion and metastasis. Indeed, peritumoral vessels are structurally and functionally abnormal, which will lead to an opposite adaptive response, aggravating the vascular anomaly, and to adaptation of the tumor cells to these conditions of increased hypoxia (Nature Reviews-Cancer; 10, 417-427, 2011). Clinical studies are ongoing to follow the antitumor effect of certain vascular-disrupting agents (VDA) based on these structural differences between normal and tumor vascularization. However, a certain prudence is imperative due to potential cardiovascular effects. It thus appears necessary to develop new antiangiogenic or antivascular compounds to treat peritumoral angiogenesis but also diseases associated with excessive abnormal angiogenesis, like age-related macular degeneration (ARMD).

The third component of tumor growth is associated with decreased partial pressure of oxygen ($pO_2$) in the center of the tumor leading to a state of intratumoral hypoxia, mentioned above. This state of hypoxia is characterized by metabolic and genetic cellular modifications leading to the activation of signaling pathways linked to survival and to activation of tumor angiogenesis. These modifications are partly the cause of phenomena of resistance to current chemotherapies. The drugs currently developed to eliminate cancer cells in hypoxia are divided into two groups: first, prodrugs bioreducible by one- or two-electron enzyme systems and second, drugs targeting factors overexpressed in the cellular response to the hypoxic state (HIFα, UPR, thioredoxin), allowing the survival of hypoxic cancer cells (Nature Reviews-Cancer, 11, 393-410, 2011). The bioreducible prodrugs of the first category are chiefly quinones (α 1-4) (apaziquone, RH1) or nitro compounds (TH-302, PR-104), acting on DNA. The major side effect of compounds of the first category shown during phase I and II clinical trials results from their toxicity and their limited extravascular penetration, effects which are even more marked as the distance of the hypoxic cells from the blood vessels increases. Other drugs which act on the thioredoxin pathway (PX12, motexafin gadolinium) and the transcription factor HIFα pathway (PX-478, PX12) are undergoing clinical evaluation.

To date, every drug used in cancer chemotherapy thus targets only one biological phenomenon at a time, and treatment specificity remains poor. It thus appears important to find new, more specific antitumor compounds acting simultaneously on the three components of tumor development.

The inventors of the present invention have discovered a novel class of compounds which respond to this need.

To that end, the inventors analyzed data concerning the biological, biochemical and genetic characteristics of cancer cells in normoxia and hypoxia, in order to find a common molecular denominator modified by cancer cells and by endothelial cells associated with abnormal peritumoral angiogenesis.

The inventors thus discovered that the analysis of all these data shows that cancer cells, in normoxia and in hypoxia, are characterized inter alia by intense production of superoxide anion, caused by strong NADPH oxidase (NOX) activity (Nature Reviews-Drug Discovery, 8, 579-591, 2009; Nature Reviews-Cancer, 12, 627-637, 2012). This superoxide anion overproduction is associated with general "redox" dysregulation, associated with low enzymatic activity (catalase, peroxiredoxin, glutathione peroxidase) degrading $H_2O_2$ and with strong activation of the thioredoxin (TRX)-thioredoxin reductase (TRX-R) system, controlling inter alia the redox state of the peroxiredoxins and the activity of HIFα. Cancer cells are thus highly dependent on "reactive oxygen species" ($O_2^{\circ-}/H_2O_2$) for their survival. This oxidative stress is regarded as an "Achilles' heel" of cancer cells. Superoxide anion overproduction is also found in active endothelial cells, in the proliferative phase, caused by high NADPH oxidase (NOX) activity during angiogenesis. The major isoform in endothelial cells is NOX2, regulated by VEGF, via the c-Src and Akt pathway, during the proliferative phase. Moreover, the inventors also discovered that in the context of a search for side effect-free anticancer prodrugs, this common molecular entity could also intervene in the activation of a prodrug to form an active drug able to act on the three tumor components, and on diseases associated with excessive angiogenesis.

Superoxide anion thus seems to be a common denominator in cancer cells under normoxic and hypoxic conditions, as well as in endothelial cells. Moreover, it can fulfill the role of an oxidative activator of prodrugs. The inventors thus selected as the criterion the overproduction of superoxide anion ($O_2^{\circ-}$) by tumor and endothelial cells, to search for a novel compound (prodrug) specifically activatable by $O_2^{\circ-}$. Screening of the ICSN chemical library made it possible to select a compound whose anticancer and antiangiogenic activities are expressed as:

- inhibition of tumor angiogenesis, with no effect on physiological angiogenesis; inhibition of "de novo" growth of vascular tubes, cytotoxicity against endothelial cells only in the growth phase;
- cytotoxicity against cancer cells in normoxia, only in the presence of $O_2^{\circ-}$;
- cytotoxicity against cancer cells in hypoxia, only in the presence of $O_2^{\circ-}$.

To determine the structure of the active product obtained after reaction of the prodrug with superoxide anion, the novel compound was exposed in vitro to superoxide anion. It forms by oxidative coupling a dimeric compound containing a quinone moiety, the anticancer activity of which appears as cytotoxicity against cancer cells in normoxia and in hypoxia.

DESCRIPTION OF THE INVENTION

The present invention relates to novel 3-aryl-4-catechol-pyrrole-N-propanol compounds and the derivatives thereof of general formula (I) below, their preparation, their specific reactivity with respect to superoxide anion, their action on cancer cells in normoxia and hypoxia, on tumor and physiological angiogenesis, their toxicity on vascular endothelial cells, their action on the formation of vascular tubes and their dimerization by oxidative coupling and action of these dimers on tumor cells, which thus may be used to treat cancer and diseases associated with excessive angiogenesis.

Thus, the present invention provides a novel compound, 3-aryl-4-catechol-pyrrole-N-propanol and the derivatives thereof, of the following general formula (I):

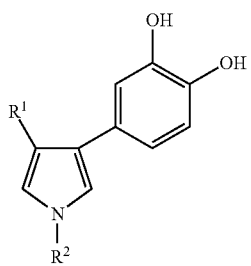

(I)

wherein:
$R^1$ represents an aryl group, in particular a phenyl, optionally substituted by one or more ($C_1$-$C_2$)alkyl groups, one or more halogens, one or more —OH, —CN or $CF_3$ groups, and a combination thereof; and
$R^2$ represents a ($C_1$-$C_6$)alkyl group or a hydroxy($C_1$-$C_6$)alkyl group or a ($C_1$-$C_4$)alkoxy($C_1$-$C_6$)alkyl group;
or a pharmaceutically acceptable hydrate or solvate thereof.

In the present invention, "pharmaceutically acceptable" means that which is useful in the preparation of a pharmaceutical composition, which is generally safe, nontoxic and neither biologically nor otherwise undesirable, and which is acceptable for both veterinary and human pharmaceutical use.

In the present invention, the term "pharmaceutically acceptable solvates" of a compound is intended to denote solvates acceptable for pharmaceutical use of the compounds according to the present invention including conventional solvates such as those formed, during the final step of the method for preparing the compounds according to the invention, with the reaction solvent(s). By way of example, mention may be made of solvates formed with water (commonly called hydrates) or with ethanol.

By "aryl" is meant, within the meaning of the present invention, an aromatic hydrocarbon group, preferably having 6 to 10 carbon atoms and comprising one or more, particularly one or two, fused rings, such as for example a phenyl or a naphthyl group. Advantageously, it is phenyl.

By "($C_1$-$C_6$)alkyl" group is meant, within the meaning of the present invention, a linear or branched saturated hydrocarbon chain having 1 to 6, in particular 1 to 4, carbon atoms. By way of example, mention may be made of the groups methyl, ethyl, propyl, isopropyl, butyl, isobutyl, sec-butyl, tert-butyl, pentyl or hexyl.

By "($C_1$-$C_2$)alkyl" group is meant, within the meaning of the present invention, a linear or branched saturated hydrocarbon chain having 1 to 2 carbon atoms. By way of example, mention may be made of the groups methyl and ethyl.

By "($C_1$-$C_4$)alkoxy" group is meant, within the meaning of the present invention, a ($C_1$-$C_4$)alkyl group, as defined above, linked to the remainder of the molecule via an oxygen atom. By way of example, mention may be made of the groups methoxy, ethoxy, propoxy, isopropoxy, butoxy or tert-butoxy.

By "hydroxy($C_1$-$C_6$)alkyl" group is meant, within the meaning of the present invention, a hydroxy group (—OH) linked to the molecule via a ($C_1$-$C_6$)alkyl group, as defined above. By way of example, mention may be made of the group 3hydroxypropyl.

By "($C_1$-$C_4$)alkoxy($C_1$-$C_6$)alkyl group is meant, within the meaning of the present invention, a ($C_1$-$C_4$)alkoxy group, as defined above, linked to the molecule via a ($C_1$-$C_6$)alkyl group, as defined above. By way of example, mention may be made of the group 3-ethoxypropyl.

By "halogen atom" is meant, within the meaning of the present invention, fluorine, chlorine, bromine and iodine atoms.

In an advantageous embodiment,
$R^1$ represents a phenyl, optionally substituted by one or more ($C_1$-$C_2$)alkyl groups, one or more halogens, one or more —OH, —CN or $CF_3$ groups, and a combination thereof; and
$R^2$ represents a ($C_1$-$C_6$)alkyl group or a hydroxy($C_1$-$C_6$)alkyl group or a ($C_1$-$C_6$)alkoxy($C_1$-$C_6$)alkyl group;
Advantageously, $R^1$ represents a phenyl and $R^2$ represents a ($C_1$-$C_6$)alkyl group or a hydroxy($C_1$-$C_6$)alkyl group or a ($C_1$-$C_4$)alkoxy($C_1$-$C_6$)alkyl group.

More advantageously, R$^1$ represents a phenyl and R$^2$ represents a (C$_1$-C$_4$)alkyl group or a hydroxy(C$_1$-C$_4$)alkyl group or a (C$_1$-C$_2$)alkoxy(C$_1$-C$_4$)alkyl group.

In a particular embodiment, le represents a phenyl and R$^2$ represents a hydroxy(C$_1$-C$_6$)alkyl group.

In particular, the compounds of the invention may be selected from the compounds of the following formulae (Ia), (Ib) and (Ic) and the pharmaceutically acceptable solvates and hydrates thereof, such as the solvate obtained with DMSO.

(Ia)
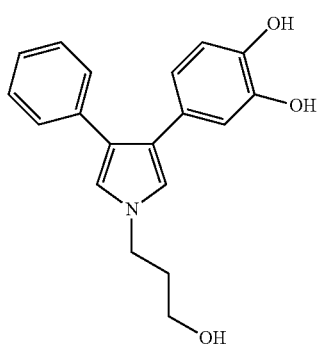

(Ib)
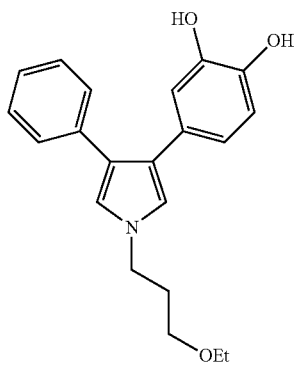

(Ic)
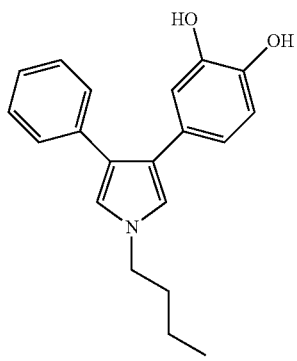

The invention also provides a compound of the following general formula (I):

(I)
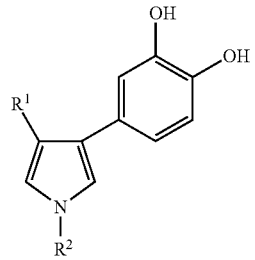

wherein:
R$^1$ represents an aryl group, in particular a phenyl, optionally substituted by one or more (C$_1$-C$_2$)alkyl groups, one or more halogens, one or more —OH, —CN or CF$_3$ groups, and a combination thereof; and
R$^2$ represents a (C$_1$-C$_6$)alkyl group or a hydroxy(C$_1$-C$_6$) alkyl group or a (C$_1$-C$_4$)alkoxy(C$_1$-C$_6$)alkyl group;
or a pharmaceutically acceptable hydrate or solvate thereof,
for use as a drug, particularly intended to treat cancer.

The compound of general formula (I) according to the invention used as drug may be selected from the compounds of the following formulae (Ia), (Ib) and (Ic):

(Ia)
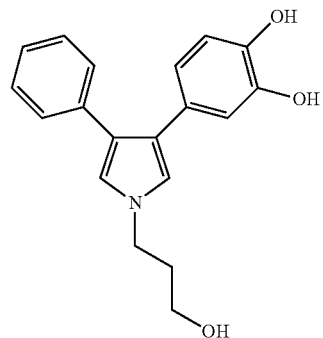

(Ib)
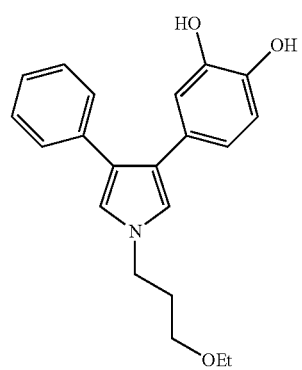

(Ic)

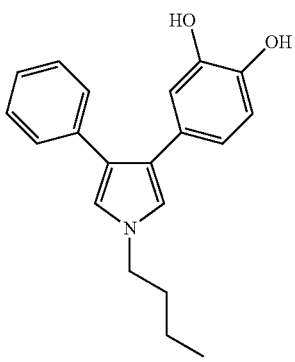

(IV)

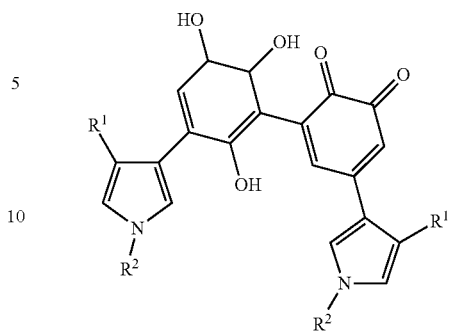

According to an aspect of the invention, the compound of general formula (I) according to the invention can dimerize, notably by oxidative coupling. In particular, dimerization of the compound according to the invention is induced in the presence of superoxide anion.

Thus, the present invention also provides the compound of general formula (I) according to the invention as a nontoxic prodrug which will be activated by its dimerization by interaction with superoxide anion.

In a particular embodiment, the present invention thus relates to the compound according to the invention for use as a prodrug activated by dimerization, notably by oxidative coupling, particularly to treat cancer and diseases associated with excessive angiogenesis.

The dimerization is carried out preferably in the presence of superoxide anion and preferably leads to at least one of the compounds of general formula (II), (III) or (IV):

(II)

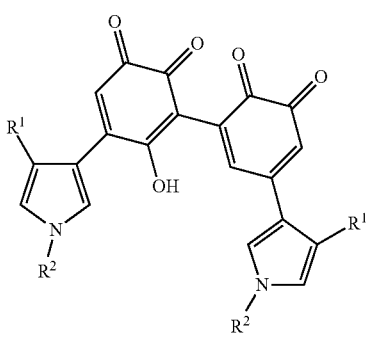

(III)

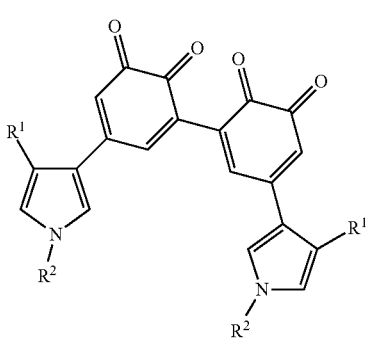

wherein $R^1$ and $R^2$ are as defined above, or a pharmaceutically acceptable hydrate or solvate thereof.

Advantageously, the dimerization leads to the compound of general formula (II). More advantageously, the dimerization leads to a compound of the following formula (IIa):

(IIa)

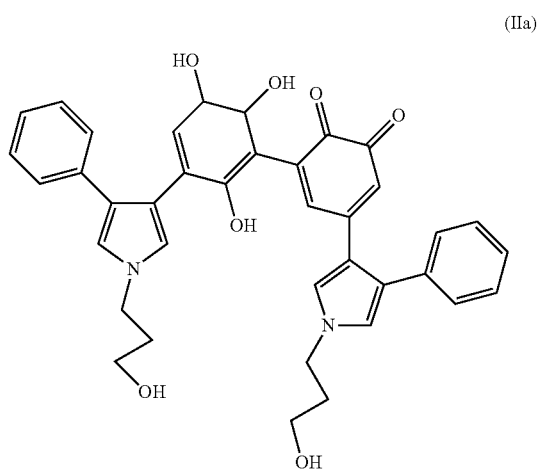 [SMILES: O=C1C=C(c2cn(CCCO)cc2-c2ccccc2)C=C(C2=C(O)C(c3cn(CCCO)cc3-c3ccccc3)=CC(O)C2O)C1=O]

Thus, the present invention also provides the compound of general formula (II) above wherein $R^1$ and $R^2$ are as defined above, or a pharmaceutically acceptable hydrate or solvate thereof.

Advantageously, the dimer of general formula (II) according to the invention is the compound of formula (IIa).

The present invention also relates to the compound of general formula (II), wherein $R^1$ and $R^2$ are as defined above, in particular the compound of formula (IIa), or a pharmaceutically acceptable hydrate or solvate thereof, for use as a drug.

The present invention also relates to the use of a compound of formula (I) or (II) according to the invention for the manufacture of a drug, particularly intended to treat cancer.

The invention also relates to a method for treating cancer, comprising the administration of an effective amount of at least one compound of formula (I) or (II) according to the invention to a patient in need thereof.

The cancer may particularly be solid or nonsolid tumors, such as melanoma, colorectal cancer, lung cancer, prostate cancer, liver cancer, breast cancer, uterine cancer, stomach cancer, pancreatic cancer, bladder cancer, ovarian cancer, head and neck cancers, brain cancer, leukemia, lymphomas (including Burkitt's lymphoma) and myelomas.

The present invention also provides a pharmaceutical composition comprising at least one compound of the following general formula (I) or (II):

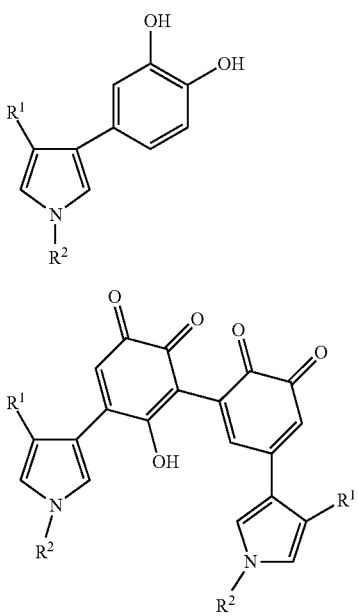

wherein:
- R¹ represents an aryl group, in particular a phenyl, optionally substituted by one or more (C₁-C₂)alkyl groups, one or more halogens, one or more —OH, —CN or CF₃ groups, and a combination thereof; and
- R² represents a (C₁-C₆)alkyl group or a hydroxy(C₁-C₆) alkyl group or a (C₁-C₄)alkoxy(C₁-C₆)alkyl group, in particular a hydroxy(C₁-C₆)alkyl group;

or a pharmaceutically acceptable hydrate or solvate thereof, and a pharmaceutically acceptable excipient.

The compounds according to the invention may be administered orally, sublingually, parenterally, subcutaneously, intramuscularly, intravenously, transdermally, locally or rectally.

In the pharmaceutical compositions of the present invention for oral, sublingual, parenteral, subcutaneous, intramuscular, intravenous, transdermal, local or rectal administration, the active ingredient may be administered in unit dosage forms, in mixture with conventional pharmaceutical carriers, to animals or to human beings. Suitable unit dosage forms include oral forms such as tablets, capsules, powders, granules and oral solutions or suspensions, sublingual and buccal dosage forms, parenteral, subcutaneous, intramuscular, intravenous, intranasal or intraocular dosage forms and rectal dosage forms.

The compounds according to the invention may be coupled with an antibody which specifically targets a tumor marker (for example a protein which, ideally, should be found only in or on tumor cells) in order to form an antibody-drug conjugate (ADC). Likewise, the compounds according to the invention may be coupled with any other vector for targeting cancer cells. Among said vectors, mention may be made of viral vectors or those derived from living beings, such as retroviruses, synthetic vectors, such as liposomes or nanoparticles and in particular titanium dioxide nanoparticles, or physical methods such as electroporation.

The compounds of the invention may be used in doses that depend on the desired effect, the duration of the treatment and the route of administration used. The person skilled in the art will also select the route of administration and the dosage best suited to the subject and to the disease to be treated. Generally, the doctor will determine the suitable dosing regimen as a function of the age, the weight and all the other factors specific to the subject to be treated.

The pharmaceutically acceptable excipient is known to the person skilled in the art and is selected according to the mode of administration of the pharmaceutical composition. By way of example, the pharmaceutically acceptable excipient may be selected from the group consisting of thinners, binders, disintegrants, colorants, lubricants, solubilizing agents, absorption-promoting agents, film-forming agents, gelling agents and mixtures thereof.

The pharmaceutical composition as described above may be useful to treat cancer.

The present invention also relates to the use of a pharmaceutical composition as described above to manufacture a drug intended to treat cancer.

The invention also relates to a method for treating cancer, comprising the administration of an effective amount of a pharmaceutical composition of the invention to a patient in need thereof.

The compound of general formula (I) according to the invention used in the pharmaceutical compositions according to the invention may be selected from the compounds of the following formulae (Ia), (Ib) and (Ic):

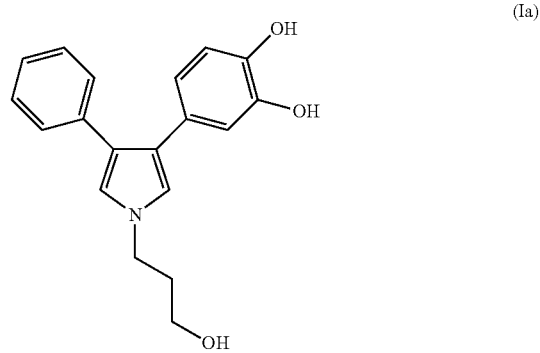

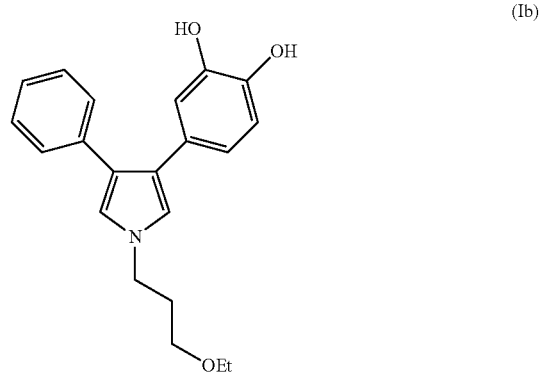

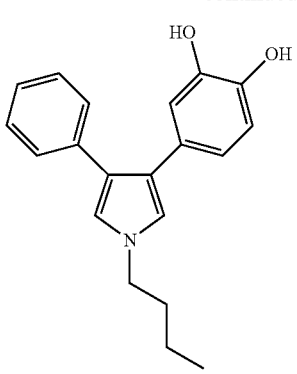
(Ic)

The present invention also provides a method for preparing a compound of the following formula (I):

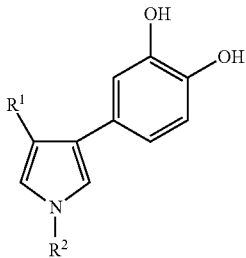
(I)

wherein:
R¹ represents an aryl group, in particular a phenyl, optionally substituted by one or more $(C_1-C_2)$alkyl groups, one or more halogens, one or more —OH, —CN or $CF_3$ groups, and a combination thereof.
R² represents a $(C_1-C_6)$alkyl group or a hydroxy$(C_1-C_6)$alkyl group or a $(C_1-C_4)$alkoxy$(C_1-C_6)$alkyl group;
or a pharmaceutically acceptable hydrate or solvate thereof, comprising, as a key step, the condensation reaction of a compound of the following formula (V):

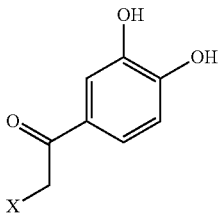
(V)

wherein X is a halogen, in particular a chlorine atom, with a compound of the following formula (VI) and a compound of the following formula (VII):

R²—NH₂      (VI)

R¹—CH₂—CHO      (VII)

wherein R¹ and R² are as defined above.

In a preferred embodiment, the compounds according to the invention are advantageously prepared under the reaction conditions described in Diagrams 1 to 5 below.

The methods for preparing the compounds according to the invention may optionally include additional protection and/or deprotection reactions so as to avoid secondary reactions well-known to the person skilled in the art. The latter has a wide choice of protecting groups which are notably described by Greene T. W. et al., Protecting Groups in Organic Synthesis, Third Edition, 1999, John Wiley & Sons.

The compounds according to the invention may further be purified by methods known to the person skilled in the art. Mention may be made, for example, of methods of purification by crystallization, chromatography or extraction.

Figure 1A:
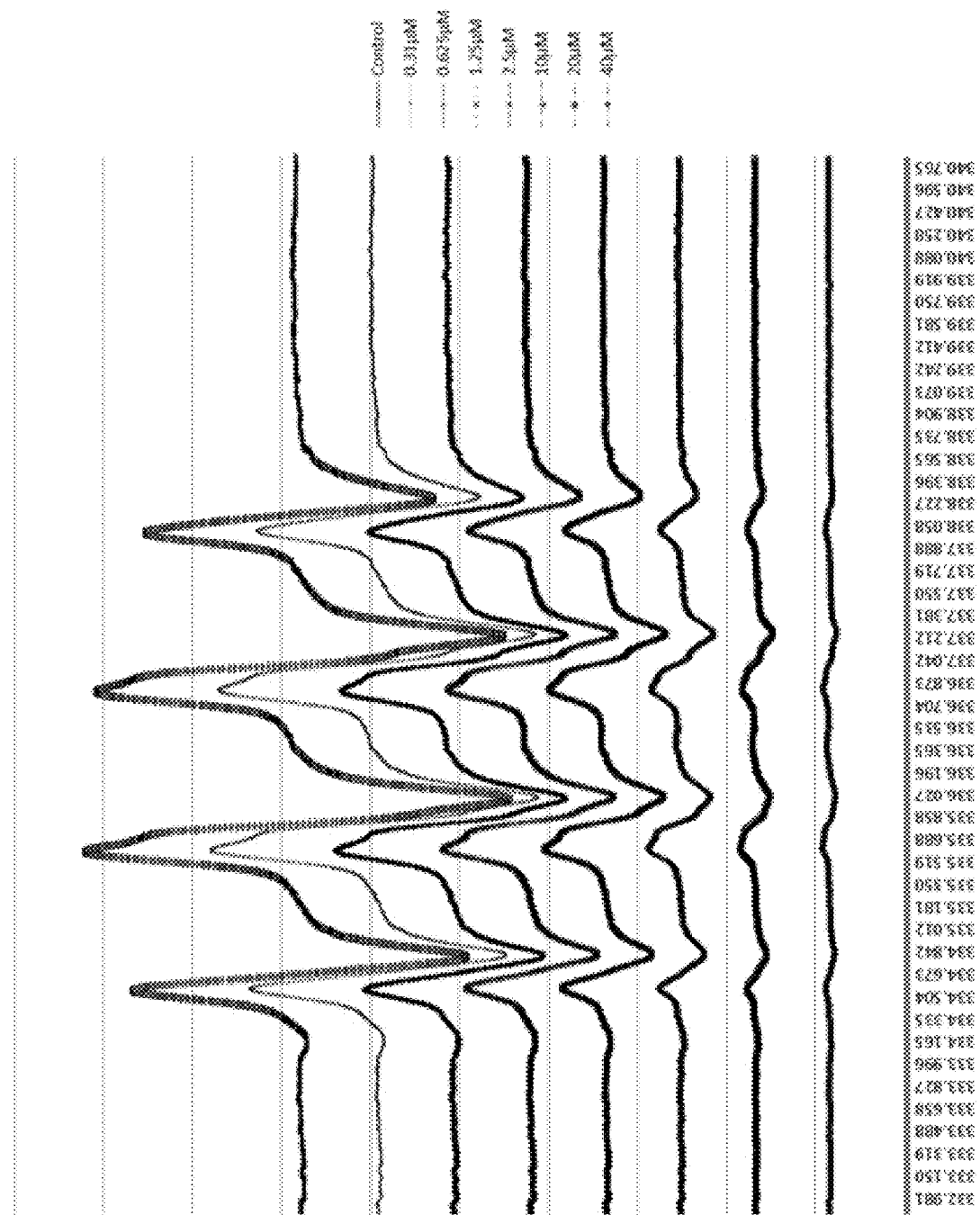
FIG. 1. Study of the reactivity of compound (1) with superoxide anion by a competition method with the trapping reagent BMPO and monitoring by electron paramagnetic resonance (EPR). Superoxide anion is produced in the organic phase by the dissolution of potassium superoxide ($KO_2$) in DMSO (A) and in the aqueous phase by the enzymatic reaction of xanthine oxidase (XO) with xanthine (X) (B).

The invention will be better understood in the light of the non-limiting examples which follow.

EXAMPLES

Abbreviations used:
AcOEt Ethyl acetate
BMPO 5-tert-Butoxycarbonyl-5-methyl-1-pyrroline-N-oxide
$IC_{50}$ Half maximal inhibitory concentration
DHE Dihydroethidium
DMSO Dimethylsulfoxide
DPBS Dulbecco's phosphate-buffered saline
$HClO_4$ Perchloric acid
HPLC High-performance liquid chromatography
$Na_2SO_4$ Sodium sulfate
NaCl Sodium chloride
$NaHCO_3$ Sodium bicarbonate
NaI Sodium iodide
PBS Phosphate-buffered saline
NMR Nuclear magnetic resonance
EPR Electron paramagnetic resonance
SOD Superoxide dismutase
RT Room temperature
THF Tetrahydrofuran Example 1

Synthesis of the Compounds of the Invention 4-(1-(3-Hydroxypropyl)-4-phenyl-1H-pyrrole-3-yl) benzene-1,2-diol) (1)

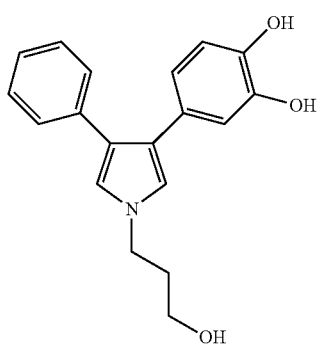 [SMILES: OCCCn1cc(-c2ccccc2)c(-c2ccc(O)c(O)c2)c1]

The compound 4-(1-(3-hydroxypropyl)-4-phenyl-1H-pyrrole-3-yl)benzene-1,2-diol) (1) was prepared by condensation of 2-chloro-3',4'-dihydroxyacetophenone with 3-aminopropan-1-ol and phenylacetaldehyde according to Diagram 1.

Diagram 1.

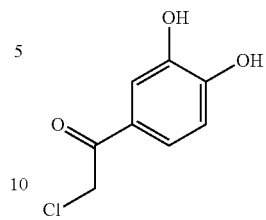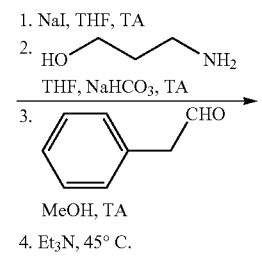

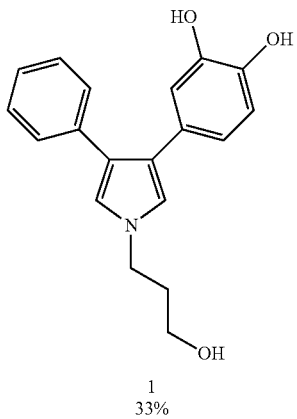

1
33%

A mixture of 2-chloro-3',4'-dihydroxyacetophenone (785 mg, 4.2 mmol) and NaI (3.15 g, 21 mmol) in THF (20 ml) is stirred for 25 minutes at RT. 3-Aminopropan-1-ol (320 4.2 mmol) then $NaHCO_3$ (1.5 g, 18 mmol) are added and the mixture is stirred for 1 hour at RT. A solution of phenylacetaldehyde (500 4.2 mmol) in methanol (30 ml) is added and the mixture is stirred for 30 minutes. Triethylamine (600 4.2 mmol) is added and the mixture is stirred for 16 hours at 45° C. The product is extracted with an ether/chloroform mixture (5:1) and the organic phase is washed with a solution of $NaHCO_3$/NaCl and brine, dried over $Na_2SO_4$, evaporated under reduced pressure and chromatographed on silica gel (elution with a gradient from pentane to THF) to give 428 mg (33%) of pyrrole 1 in the form of an amorphous semi-solid. $^1H$ NMR ($CD_3OD$; 300 MHz) δ(ppm) 7.15-6.92 (5 H; m); 6.68 (1 H; d; J=2.4 Hz); 6.59 (1 H; d; J=2.4 Hz); 6.56-6.50 (2 H; m); 6.44(1 H; dd; J=8.1; 2.1 Hz); 3.89 (2 H; t; J=6.9 Hz); 3.48 (2 H; t; J=6.9 Hz); 1.89 (2 H; quint; J=6.9 Hz). $^{13}C$ NMR ($CD_3OD$; 75 MHz) δ(ppm) 145.8; 144.4; 138.0; 129.9; 129.2; 129.0; 126.1; 124.5; 124.1; 121.2; 121.1; 121.0; 117.0; 116.1; 59.7; 47.0; 35.3. IR (neat) $v_{max}$ $cm^{-1}$ 3337; 2946; 1599; 1542; 1435; 1395; 1354; 1286; 1257; 1190; 1163; 1111; 1057; 770; 700. HRMS (ES) (m/z) $[M+H]^+$ calculated for $C_{19}H_{20}NO_3$ 310.1443; found 310.1457.

3(3(2,3Dihydrobenzo[b][1,4]dioxin-6-yl)-4phenyl-1H-pyrrole-1-yl)propan-1-ol (2)

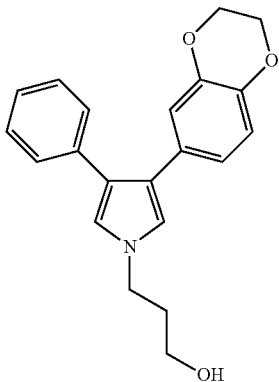 [SMILES: OCCCn1cc(-c2ccccc2)c(-c2ccc3c(c2)OCCO3)c1]

The compound 3-(3-(2,3-dihydrobenzo[b][1,4]dioxin-6-yl)-4-phenyl-1H-pyrrole-1-yl)propan-1-ol (2) was prepared by condensation of 6-chloroacetyl-1,4-benzodioxane with 3-aminopropan-1-ol and phenylacetaldehyde according to Diagram 2.

Diagram 2.

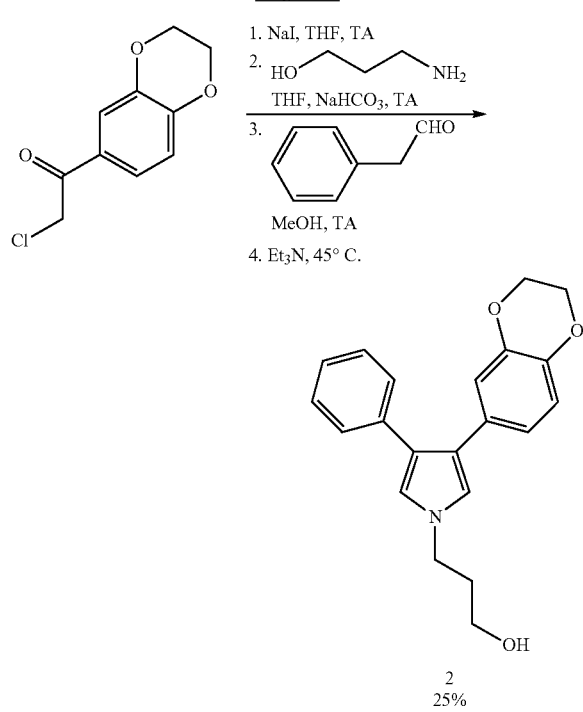

2
25%

A mixture of 6chloroacetyl-1,4benzodioxane (1.0 g, 4.56 mmol) and NaI (3.453 g, 22.8 mmol) in THF (23 ml) is stirred for 25 minutes at RT. 3-Aminopropan-1-ol (350 µL, 4.56 mmol) then NaHCO₃ (1.64 g, 19.6 mmol) are added and the mixture is stirred for 1 hour at RT. A solution of phenylacetaldehyde (566 µL, 4.56 mmol) in methanol (32 ml) is added and the mixture is stirred for 30 minutes. Triethylamine (636 µL, 4.56 mmol) is added and the mixture is stirred for 16 hours at 45° C. The product is extracted with an ether/chloroform mixture (5:1) and the organic phase is washed with a solution of NaHCO₃/NaCl and brine, dried over Na₂SO₄, evaporated under reduced pressure and chromatographed on silica gel (heptane/AcOEt 6:4) to give 394 mg (25%) of pyrrole 2.

3-(3,4-Diphenyl-1H-pyrrol)propan-1-ol (3)

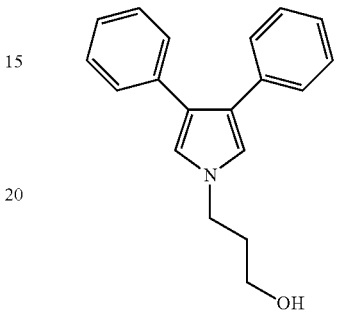

The compound 3-(3,4-diphenyl-1H-pyrrol)propan-1-ol (3) was prepared by condensation of 2-bromoacetophenone with 3-aminopropan1-ol and phenylacetaldehyde according to Diagram 3.

Diagram 3.

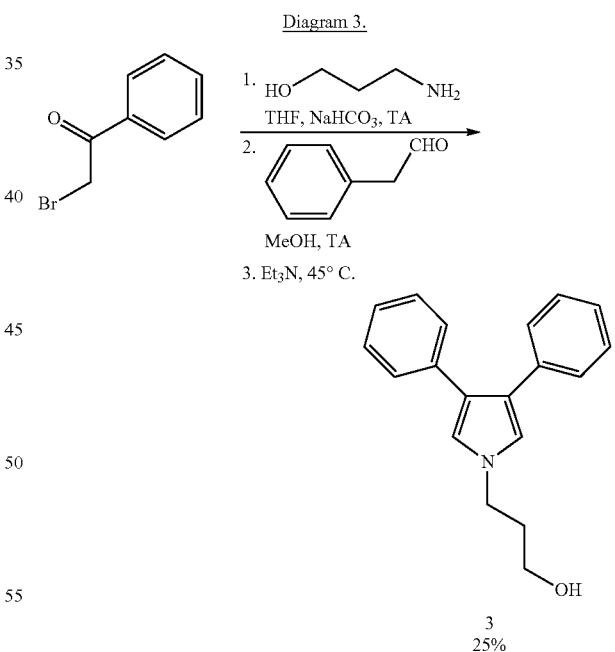

3
25%

To a solution of 2-bromoacetophenone (597.2 mg; 3 mmol) in 15 ml of THF stirred at room temperature, 3-aminopropan1-ol (233.9 µL; 3 mmol) then sodium hydrogen carbonate (1.086 g; 12.9 mmol) are added. After 1 hour of stirring at room temperature, a solution of 90% phenylacetaldehyde (390 µL; 3 mmol) in 21.4 ml of methanol is added dropwise. After 30 minutes of stirring, triethylamine (418.2 µL; 3 mmol) is added. The resulting solution is stirred at 45° C. for 20 hours. After adding water, the product is extracted with dichloromethane. Washing the organic phase with a 1:1 mixture of saturated NaHCO$_3$ and NaCl solutions, followed by drying over MgSO$_4$ then evaporation and placement under the vacuum of a vane pump produces the crude product in the form of an orange oil (881 mg). After chromatography on silica (60A thickened with heptane/AcOEt 1:1, column height 25 cm, diameter 2 cm, introduction of ethyl acetate) the collected fractions make it possible to estimate by NMR a yield of about 25%. The pure fraction taken up in acetonitrile and washed with pentane produces 44 mg of pure product (orange oil) for the analyses. $^1$H NMR (CDCl$_3$; 500 MHz) δ(ppm) 2.05 (m; 2 H); 3.70 (t; J=6.0 Hz; 2 H); 4.05 (t; J=6.9 Hz; 2 H); 6.79 (sl; 2 H); 7.18 (m; 2 H); 7.27 (m; 4 H). 7.31 (m; 4 H). $^{13}$C NMR (CDCl$_3$; 125 MHz) δ(ppm) 33.9; 46.3; 59.6; 120.4; 123.3; 125.6; 128.2; 128.5; 136.1. IR (film) v$_{max}$ cm$^{-1}$ 3315; 3057; 2932; 1697; 1601. MS (ES$^+$) (m/z) 278 (100%. [M+H]$^+$). HRMS (ES) (m/z) (278.1542; [M+H]$^+$); calculated for C$_{19}$H$_{20}$NO: 278.1545.

4-(1-(3-Ethoxypropyl)-4-phenyl-1H-pyrrole-3-yl) benzene-1,2-diol (4)

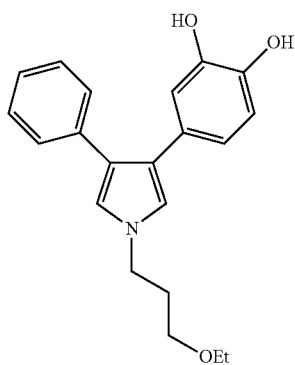 [SMILES: CCOCCCn1cc(-c2ccccc2)c(-c2ccc(O)c(O)c2)c1]

The compound 4-(1-(3-ethoxypropyl)-4-phenyl-1H-pyrrole-3-yl)benzene-1,2diol (4) was prepared by condensation of 2-chloro-3',4'-dihydroxyacetophenone with 3-ethoxypropylamine and phenylacetaldehyde according to Diagram 4.

Diagram 4.

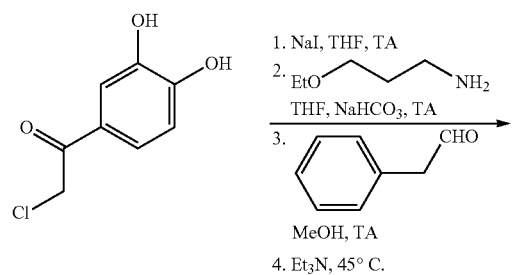

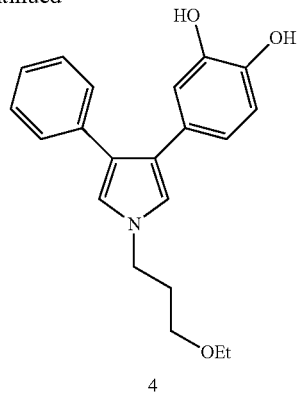

A mixture of 2-chloro-3',4'-dihydroxyacetophenone (1.0 g, 5.2 mmol) and NaI (3.94 g, 26 mmol) in THF (25.9 ml) is stirred for 25 minutes at RT. 3-Ethoxypropylamine (630 µL, 5.2 mmol) then NaHCO$_3$ (1.88 g, 22.4 mmol) are added and the mixture is stirred for 1 hour at RT. A solution of phenylacetaldehyde (650 µL, 5.2 mmol) in methanol (37 ml) is added and the mixture is stirred for 30 minutes. Triethylamine (720 µL, 5.2 mmol) is added and the mixture is stirred for 16 hours at 45° C. The product is extracted with an ether/chloroform mixture (5:1) and the organic phase is washed with a solution of NaHCO$_3$/NaCl and brine, dried over Na$_2$SO$_4$, evaporated under reduced pressure and chromatographed on silica gel.

4-(1-(3-Hydroxypropyl)-4-butyl-1H-pyrrole-3-yl) benzene-1,2-diol) (5)

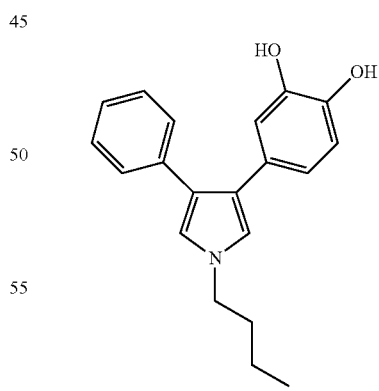

The compound 4-(1-butyl-4-phenyl-1H-pyrrole-3-yl)benzene-1,2-diol) (1) was prepared by condensation of 2-chloro-3',4'-dihydroxyacetophenone with 3-aminopropan-1-ol and phenylacetaldehyde according to the following Diagram.

Diagram 5.

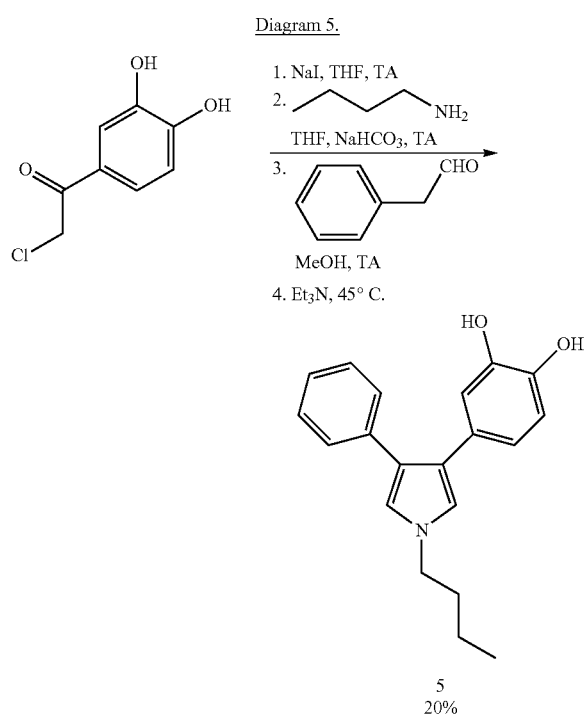

5
20%

A mixture of 2-chloro-3',4'-dihydroxyacetophenone (279.9 mg, 1.5 mmol) and NaI (224.9 mg, 1.5 mmol) in THF (7.5 ml) is stirred for 30 minutes at RT. Butylamine (148 µL, 1.5 mmol) then NaHCO$_3$ (542.8 mg, 6.46 mmol) are added and the mixture is stirred for 1 hour at RT. A solution of 90% phenylacetaldehyde (195 µL, 1.5 mmol) in methanol (10.7 ml) is added dropwise and the mixture is stirred for 30 minutes. Triethylamine (209 µL, 1.5 mmol) is added and the mixture is stirred for 20 hours at 45° C. After adding water, the product is extracted with an ether/chloroform mixture (5:1) and the organic phase is washed with saturated NaHCO$_3$/saturated NaCl solution (1:1) and dried over Na$_2$SO$_4$, evaporated under reduced pressure to give 511 mg of black oil containing 20% of pyrrole 1 (estimate by NMR). After chromatography on silica gel (elution with a 7:3→1:1 heptane/ethyl acetate gradient) the product was purified by HPLC. A pure sample of 1 was obtained in the form of an orange oil. $^1$H NMR (CDCl$_3$; 500 MHz) δ(ppm) 7.19-7.33 (4 H; m); 7.15 (1 H; m); 6.66-6.78 (5 H; m); 3.88 (2 H; t; J=7.6 Hz); 1.81 (2 H; quint; J=7.6 Hz); 1.40 (2 H; sext; J=7.6 Hz); 0.96 (3 H; t; J=7.6 Hz). $^{13}$C NMR (CDCl$_3$; 125 MHz) δ(ppm) 143.1; 141.8; 136.2; 129.6; 128.5 (2 C); 128.3 (2 C); 125.6; 122.9; 122.6; 121.5; 120.2; 120.0; 115.7; 115.4; 49.7; 33.6; 20.2; 13.8. IR (neat) ν$_{max}$ cm$^{-1}$ 3372; 2958; 1673; 1601. MS (ES) (m/z) 306 [M−H]$^-$. HRMS (ES) (m/z) [M−H]$^-$ calculated for C$_{20}$H$_{20}$NO$_2$ 306.1494; found 306.1483.

Example 2

Reactivity of Compound (1) with Superoxide Anion In Vitro; Study by Electron Paramagnetic Resonance (EPR) in the Presence of BMPO. Determination of IC$_{50}$ The reactivity of compound (1) with superoxide anion in the organic phase was studied by EPR at room temperature using a competition method with the superoxide trapping reagent BMPO (5-tent-butoxycarbonyl-5-methyl-1-pyrroline N-oxide) (FIG. 1A). The superoxide anion source is potassium salt (KO$_2$) used at 5 mM in DMSO after ultrasound-assisted dissolution. The concentrations used for compound (1) are between 0.31 and 40 µM. The trapping reagent BMPO is used at a final concentration of 25 mM. These experiments were carried out with a MiniScope MS 100 EPR spectrometer (Magnettech GmbH, Germany), operating at a frequency of 9.5 GHz (X-band) with the following parameters: magnetic field: 336.0±9.9 mT; sweep time: 20 s; sampling: 4096 points; modulation amplitude: 0.10 mT; modulation frequency: 100 kHz; gain: 900; microwave power: 100 mW. The inhibition of the formation of the BMPO superoxide adduct, expressed as a decrease in the intensity of the EPR spectrum of this species, is dependent on the amount of compound (1) applied and produces a half maximal inhibitory concentration (IC$_{50}$) of 2.5 µM.

Figure 1B:
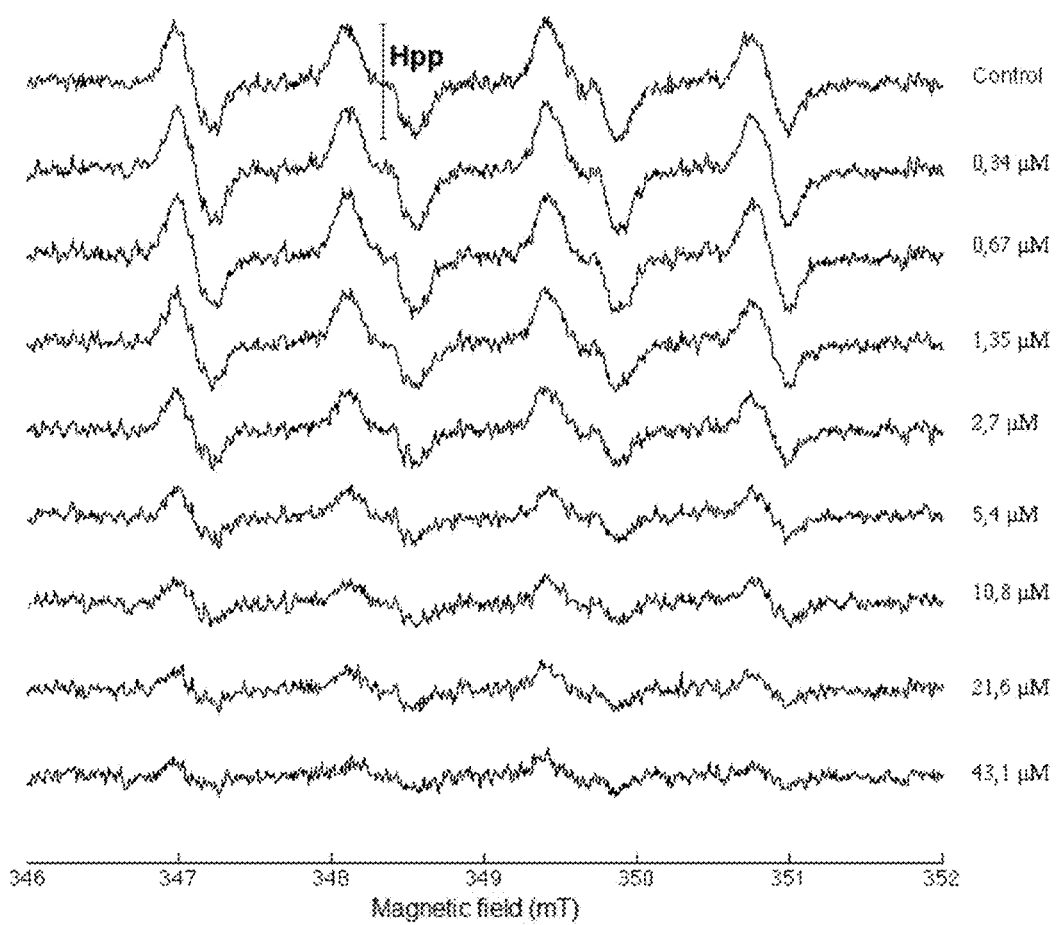

The reactivity of compound (1) with superoxide anion in the aqueous phase was also studied by EPR at room temperature using the same competition method with the trapping reagent BMPO at 50 mM (FIG. 1B). In this case, superoxide anion is produced by enzymatic reaction of xanthine oxidase (XO, 53 mU/mL) with xanthine (X, 250 µM) in PBS (pH 7.4) containing 0.1 mM ethylenediaminetetraacetic acid (EDTA). The concentrations used for compound (1) are between 0.34 µM and 43.1 µM. These experiments were carried out with an ELEXSYS E500 EPR spectrometer (Bruker, Wissembourg, France), operating at a frequency of 9.82 GHz (X-band) with the following parameters: magnetic field: 349.0 ±6.6 mT; sweep time: 41.94 s; sampling: 1024 points; time constant: 40.96 ms; conversion time: 40.96 ms; modulation amplitude: 0.10 mT; modulation frequency: 100 kHz; gain: 60 dB; microwave power: 10 mW. The inhibition of the formation of the BMPO superoxide adduct, expressed as a decrease in the intensity of the EPR spectrum of this species after 10 minutes of incubation, depends on the concentration of compound (1) used; an IC$_{50}$ of 3.2 µM is measured.

A direct reaction between compound (1) and the BMPO superoxide adduct was excluded by confirming that the stability of the BMPO adduct, formed by preincubation with the X/XO system, is not modified in the presence of compound (1) (result not shown).

Example 3

Figure 2A:
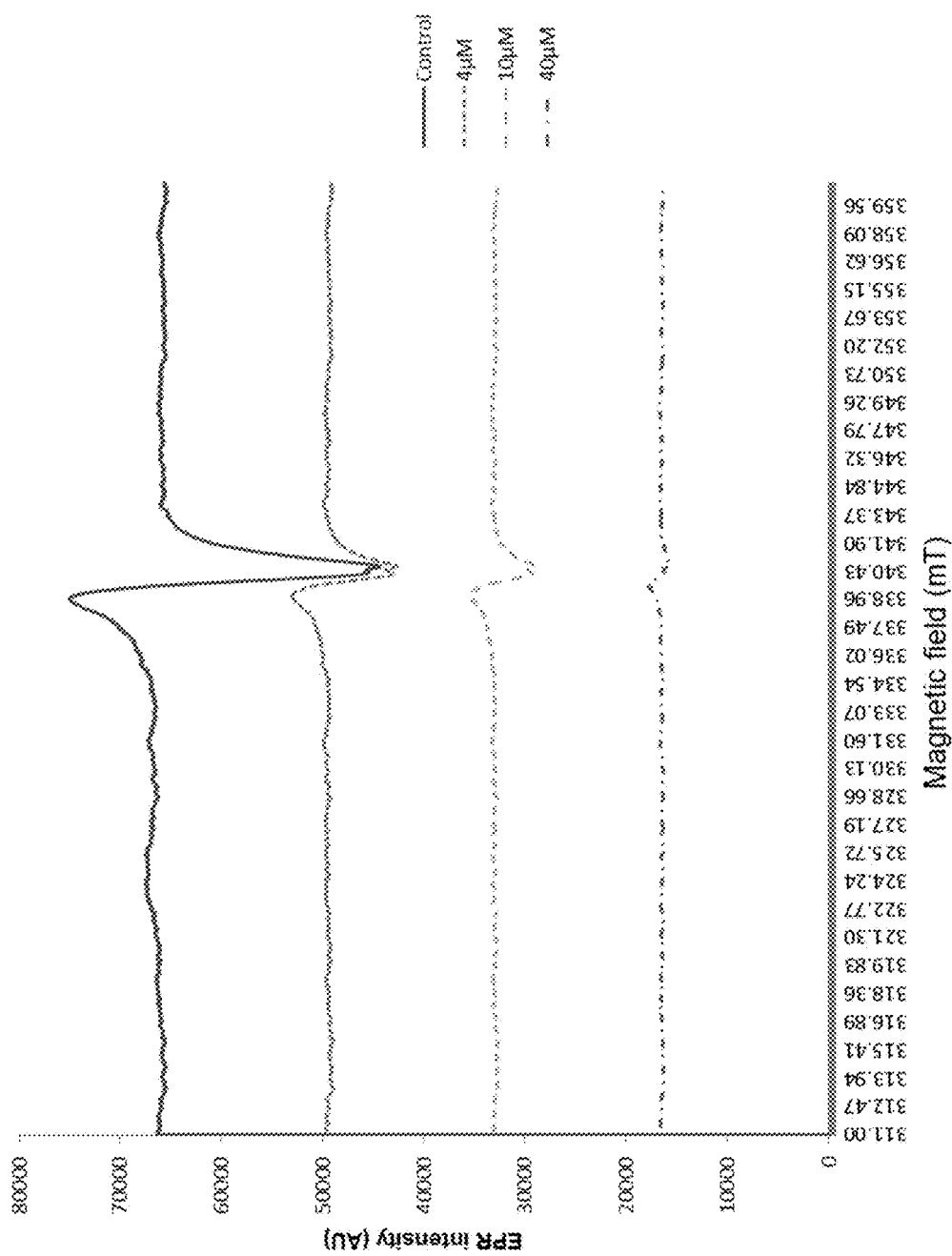
FIG. 2. Study by electron paramagnetic resonance (EPR) of the reaction of compound (1) with superoxide anion, produced by the dissolution by sonication of $KO_2$ in DMSO: A—Monitoring of the decrease in the EPR signal of $O2^{\circ-}$ at liquid-nitrogen temperature (77 K) as a function of the concentration of compound (1) added; B—EPR spectrum of the radical intermediate observed at room temperature and the simulation of same.

Reactivity of Compound (1) with superoxide Anion In Vitro: Study by Paramagnetic Resonance Electronic (EPR) of the Disappearance of the O2$^{\circ-}$ Signal in the Presence of Compound (1), and Demonstration of the Formation of a Radical Intermediate In order to follow the direct interaction of compound (1) with superoxide anion, solid potassium superoxide (KO$_2$) was dissolved by sonication in DMSO (final concentration 2.5 mM), then mixed with compound (1) and immediately cooled by immersion in liquid nitrogen. EPR analysis at 77 K (liquid nitrogen) was carried out with a MiniScope MS 100 EPR spectrometer, operating at a frequency of 9.5 GHz (X-band) with the following parameters: magnetic field: 336.0±49.8 mT; sweep time: 20 s; sampling: 4096 points; modulation amplitude: 0.10 mT; modulation frequency: 100 kHz; gain: 900; microwave power: 6 mW. The results show a decrease in the EPR signal of superoxide anion, dependent on the concentration of compound (1) (FIG. 2A).

Figure 2B:
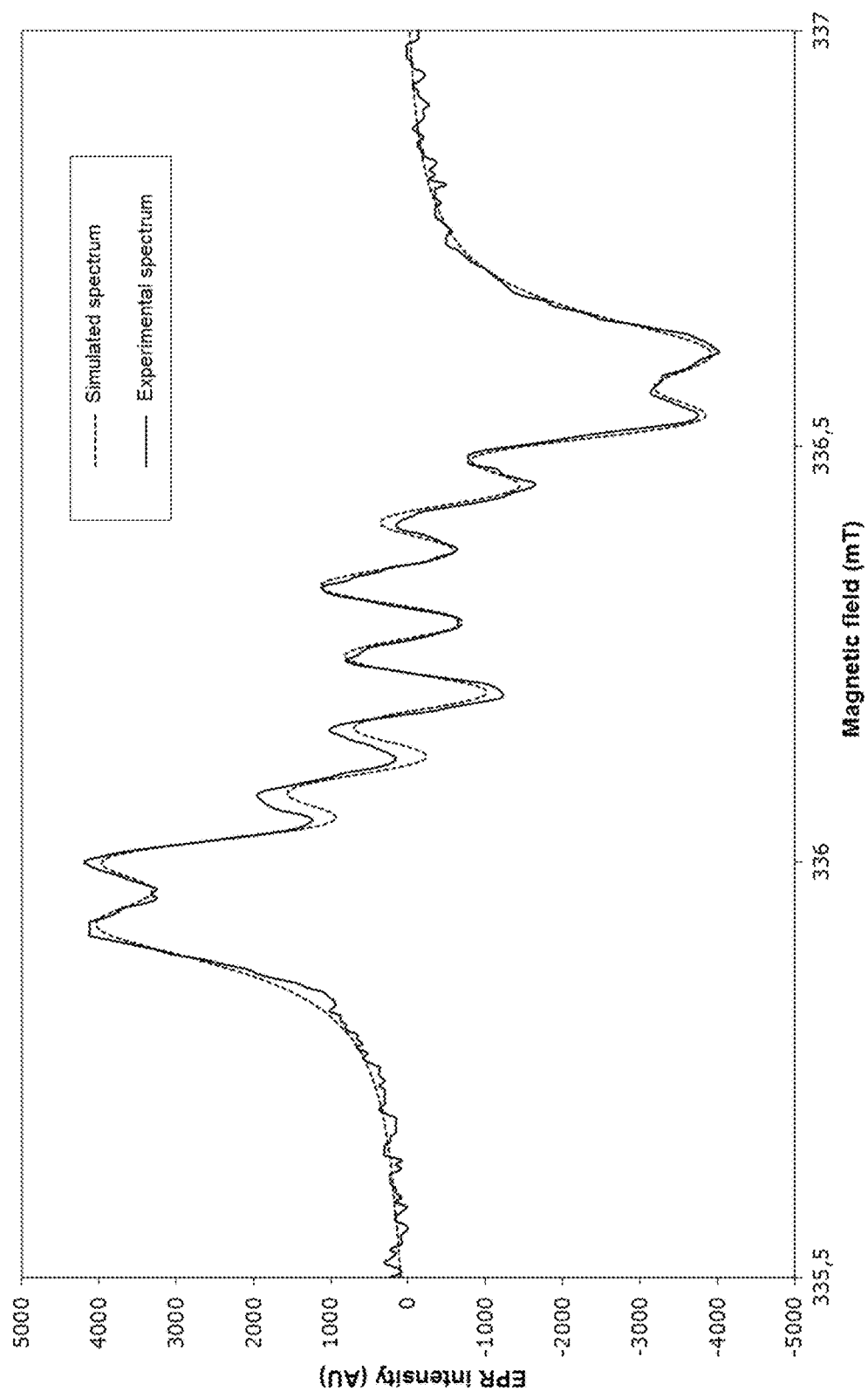

The EPR spectrum of the radical formed by reaction of compound (1) (40 µM) with superoxide anion (0.5 mM $KO_2$ dissolved in DMSO by sonication) was recorded at room temperature (FIG. 2B). This EPR analysis was carried out with a MiniScope MS 100 EPR spectrometer, operating at a frequency of 9.5 GHz (X-band), with the following parameters: magnetic field: 336.0±1.9 mT; sweep time: 20 s; sampling: 4096 points; modulation amplitude: 0.05 mT; modulation frequency: 100 kHz; gain: 900; microwave power: 100 mW. This phenoxyl radical spectrum, centered around g =2.00, was simulated using the Rockenbauer and Korecz software (Rockenbauer, A.; Korecz, L. Automatic computer simulations of ESR spectra. *Appl. Magn. Reson.* 10:29-43; 1996), taking into account four proton coupling constants equal to 0.33, 0.16, 0.08 and 0.08 mT. The most likely attribution of these couplings corresponds to three protons of the catechol aromatic system and one proton of the pyrrole. The couplings to the other proton and to the nitrogen of the pyrrole ring are not resolved.

Example 4

Formation of a Quinone Intermediate by Reaction of Compound (1) with Superoxide Anion ($O_2^{\circ-}$)

Figure 3A:
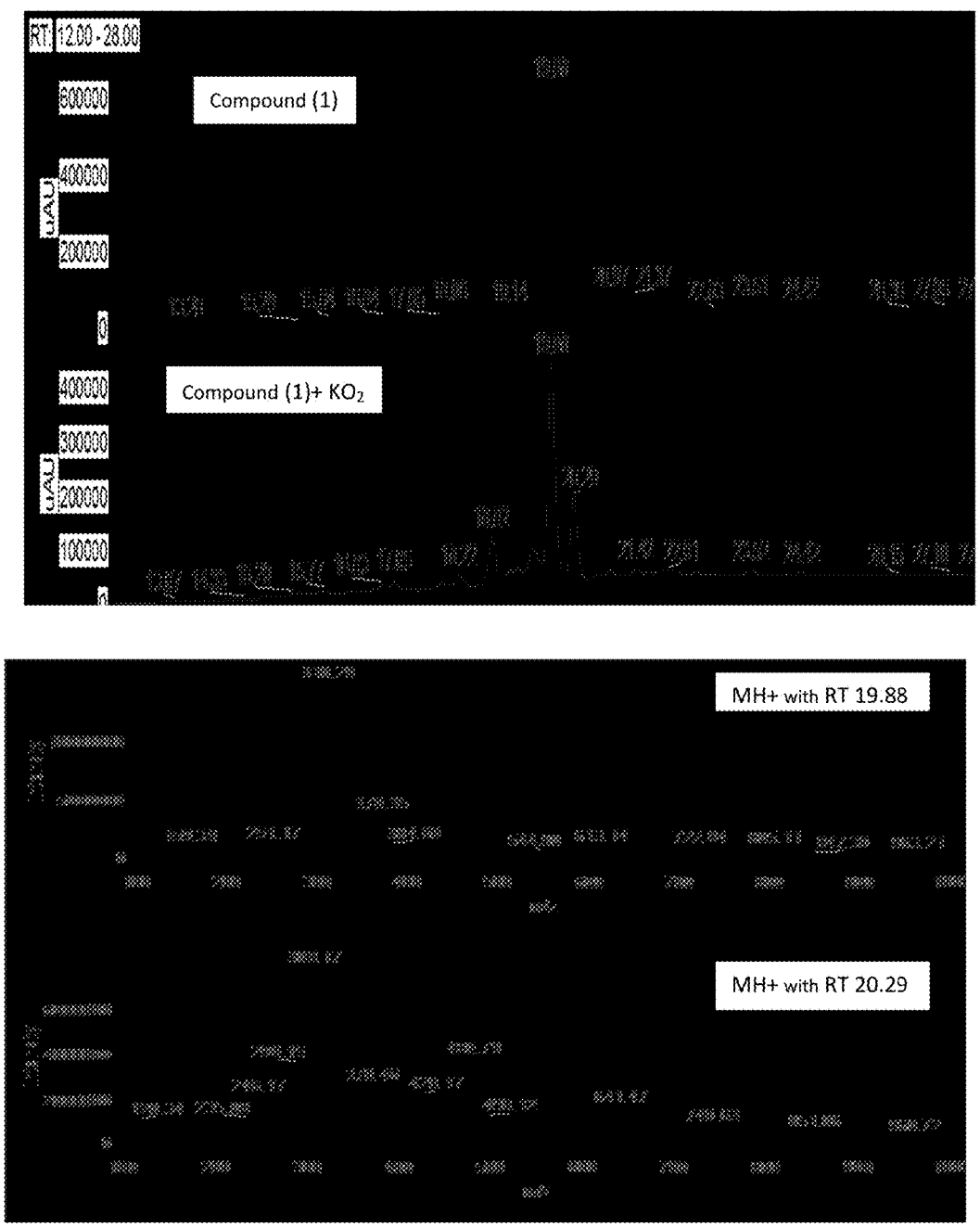
FIG. 3. Formation of a quinone intermediate after reaction of compound (1) with superoxide anion ($KO_2$) in the organic phase (DMSO). Analysis by HPLC-MS on LC-TRAP (A) and 500 MHz NMR ($^{13}C$) (B).

The product of the oxidation of compound (1) by superoxide anion in the organic phase ($KO_2$ dissolved by sonication in DMSO) was characterized by HPLC (LC-Trap; Surveyor, Thermo). The reaction mixture (final volume 200 µL) consists of compound (1) at $1.6 \times 10^{-3}$ M (20 µL in DMSO), treated or not with $KO_2$, 10 µL (5 mM). The reaction mixture (20 µL) was injected on a Gemini column (C18, 2×150 mm, 5 Phenomenex), with initially 98% solvent A (A=$H_2O$; 0.1% formic acid), and 2% solvent B (acetonitrile; 0.1% formic acid), at a flow rate of 0.2 ml/min. After 5 minutes, the gradient passed to 0% A and 100% B for 20 minutes. The results obtained (FIG. 3A) show that compound (1) having a retention time equal to 19.88 and m/z =310.20 (MH+) is partially transformed into compounds having inter alia a retention peak equal to 20.29 and m/z=308.17 (MH+). These results suggest the oxidation of compound (1) by superoxide anion.

Figure 3B:
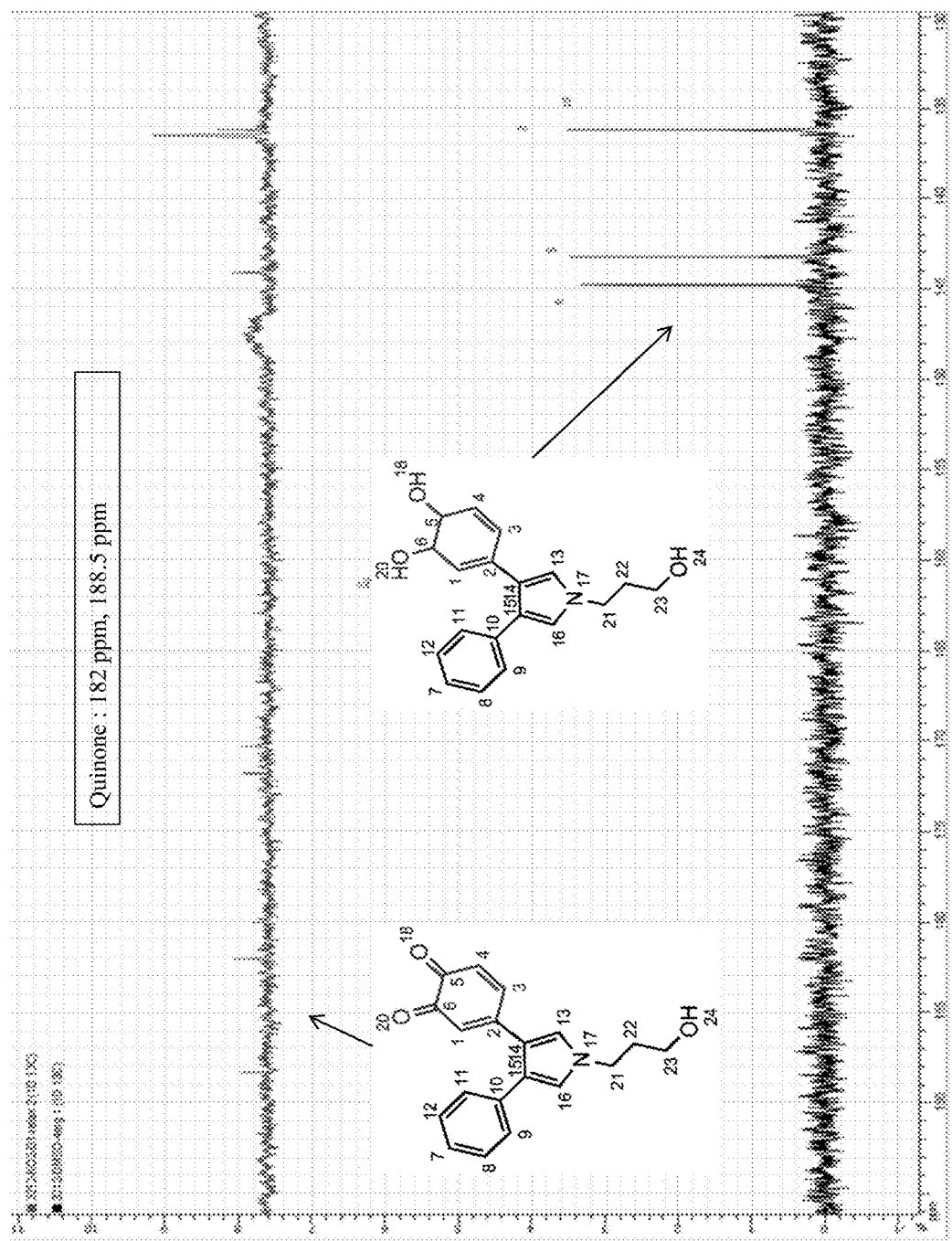

The oxidation product of compound (1) by superoxide anion generated by $KO_2$ was analyzed by $^{13}C$ NMR on a Brucker AVANCE-500 spectrometer. The results (FIG. 3B) show suppression of the signals corresponding to carbons 5 and 6 of compound (1) and the formation of two signals with a chemical shift of 182 ppm and 188.5 ppm, characteristic of quinones for the two carbons 5 and 6 of compound (1) treated.

Example 5

Formation of a Dimeric Compound MH+=631 "In Vitro" by Reaction of Compound (1) with Superoxide Anion ($O_2^{\circ-}$) or at pH=pKa=8.89

The dimeric compound was formed after reaction of compound (1) ($0.3 \times 10^{-3}$ M) with superoxide anion generated by the xanthinexanthine oxidase complex, in PBSEDTA solvent.

Figure 4A:
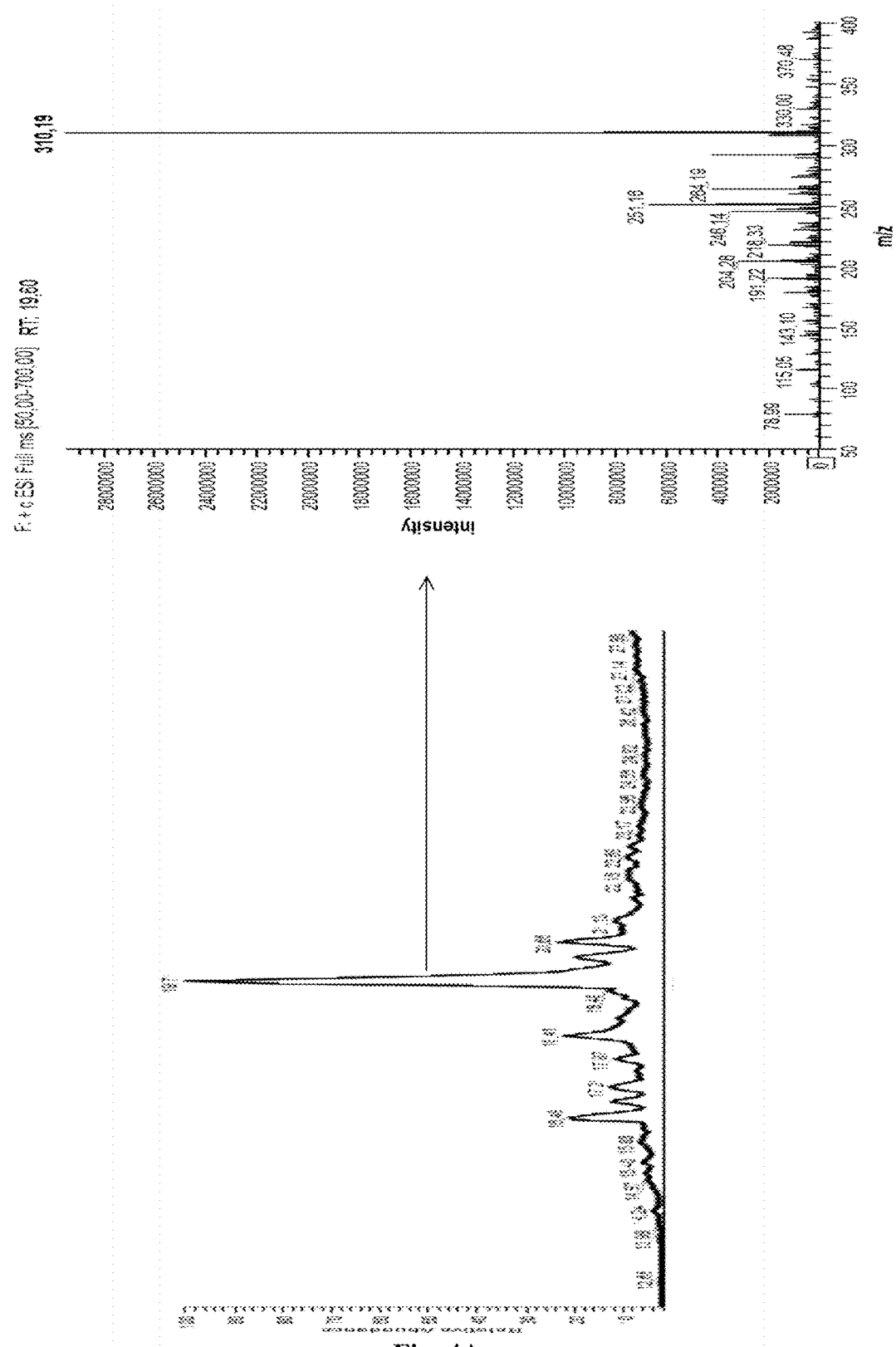
FIG. 4. Formation of a dimeric compound by oxidative coupling in the presence (A) of superoxide anion produced by xanthine oxidase (analysis by HPLC-TRAP) or (B) at pH equal to pKa (8.89) (analysis by UHPLC). UV spectrum of the dimeric compound MH+ 631 (C) obtained by oxidative coupling at pH 9.4.

The formation of the dimeric compound MH+ 631 was monitored on an HPLC Surveyor (Thermo), coupled to an LCQ Deca (Thermo). The reaction mixture (10 µL) was injected on a Gemini column (C18, 2×150 mm, 5 Phenomenex), with initially 98% solvent A (A=$H_2O$; 0.1% formic acid) and 2% solvent B (acetonitrile; 0.1% formic acid), at a flow rate of 0.2 ml/min. After 5 minutes, the gradient passed to 0% A, 100% B for 20 minutes. The results obtained (FIG. 4A) show that compound (1) having a retention time equal to 19.71 and m/z=310.19 (MH+) is transformed into compounds having inter alia a retention peak equal to 20.63 and m/z=631.16 (MH+). In the presence of superoxide dismutase and catalase, the dimeric compounds are not formed (results not shown). These results support the dimerization of compound (1) in the presence of superoxide anion.

Figure 4B:
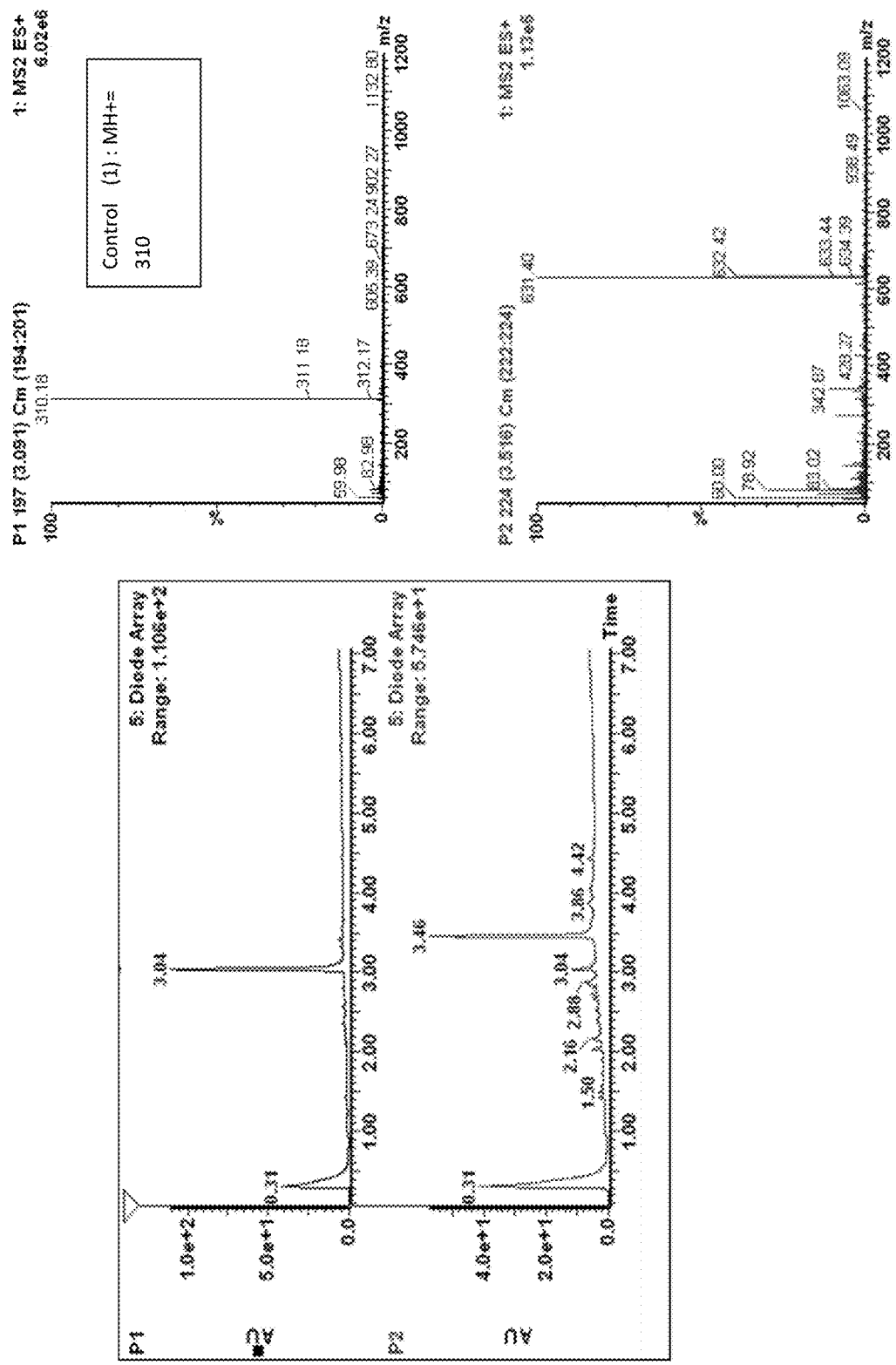

In order to carry out the dimerization of compound (1) by oxidative coupling at pH equal to the pKa value of the compound, the theoretical pKa was determined by quantum calculations using the Gaussian03 software (Gaussian, Inc., Wallingford Conn., 2004) and a method adapted from Liptak et al. (J. Am. Chem. Soc. 2002, 124, 6421-6427), notably by modifying the default values of the PCMDOC, RADII, SCFVAC and TSARE parameters to make them compatible with the values of Gaussian98, the software used in the original publication. The pKa value obtained by this method was 8.89, the value which was then used to adjust the pH of a Tris-HCl 0.15 M, DMSO: 10% solution for the dimerization reaction of compound (1) at $0.3 \times 10^{-2}$ M final. The reaction mixture (10 µL) was chromatographed by UHPLC (Waters, TQD, PDA, ELSD), on an HSS C18 column (Waters, 2.1×50 mm; 1.8 µm) with a solvent gradient initially containing 95% A ($H_2O$, 0.1% formic acid) and 5% B (acetonitrile, 0.1% formic acid) then 100% solvent B in 6.5 minutes, at a flow rate of 0.6 ml per minute. The results, presented in FIG. 4B, show that compound (1), having a single peak at a retention time ($t_R$) of 3.04 and m/z=310.19 (corresponding to the MH+ ion), is transformed into a compound whose retention time is $t_R$=3.46 and m/z=631.40 (MH+). These results suggest that compound (1) is oxidized and dimerizes.

In order to obtain the dimer MH+ 631 in sufficient quantity to determine its structure, the oxidative coupling of 12 mg of compound (1) in Tris-HCl, 0.15 M, pH 9.4, DMSO solution (15% final) was carried out. After 48 hours, the reaction was stopped by several drops of 0.1 N HCl. The dimer MH+ 631 was separated on a C18 column, preparative HPLC (ACN, $H_2O$, 0.1% formic acid), followed by extraction in the presence of a mixture of acetonitrile (50%) and ether (50%). After evaporation, the dimeric compound was dissolved in deuterated acetonitrile and analyzed by NMR ($^1H$, $^{13}C$, COSY, HMBC, HSQC) (Brucker 600):

$^1H$ NMR ($CD_3CN$; 263 K; 600 MHz) δ(ppm) ~7.5 (1 H; sl); 7.33 (2 H; m); 7.26 (3 H; m); 7.17 (2 H; m); 7.13 (2 H; m); 7.05 (1 H; m); ~7.0 (2 H; sl); 6.78 (2 H; m); 6.77 (1 H; s); 6.55 (1 H; s); 6.51 (1 H; d; J=2 Hz); 6.42 (1 H; d; J=2 Hz); 6.02 (1 H; s); 3.87 (2 H; t; J=7.2 Hz); 3.84 (2 H; t; J=7.2 Hz); 3.42; (2 H; t; J=5.4 Hz); 3.31; (2 H; t; J=5.4 Hz); 3.05 (1 H; sl); 2.97 (1 H; sl); 1.82; (2 H; quint; J=6.6 Hz); 1.70; (2 H; quint; J=6.6 Hz).

$^{13}C$ NMR ($CD_3CN$; 263 K; 150 MHz) δ(ppm) 188.1; 182.8; 151.6; 145.1; 144.3; 143.1; 137.1; 136.1; 129.8; 129.54; 129.48; 129.4; 129.1; 128.8; 128.2; 127.3; 126.0; 125.4; 124.0; 123.8; 123.3; 123.1; 123.0; 122.6; 122.2; 120.6; 118.1; 114.5; 58.9; 58.8; 47.1; 46.7; 34.9; 34.2.

The proposed structure of the dimer is as follows:

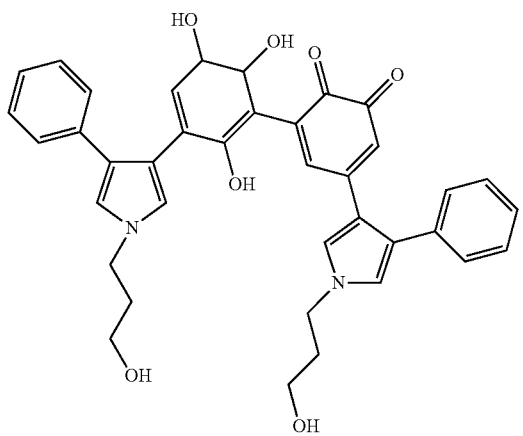 [SMILES: O=C1C=C(c2cn(CCCO)cc2-c2ccccc2)C=C(C2=C(O)C(c3cn(CCCO)cc3-c3ccccc3)=CC(O)C2O)C1=O]

Figure 4C:
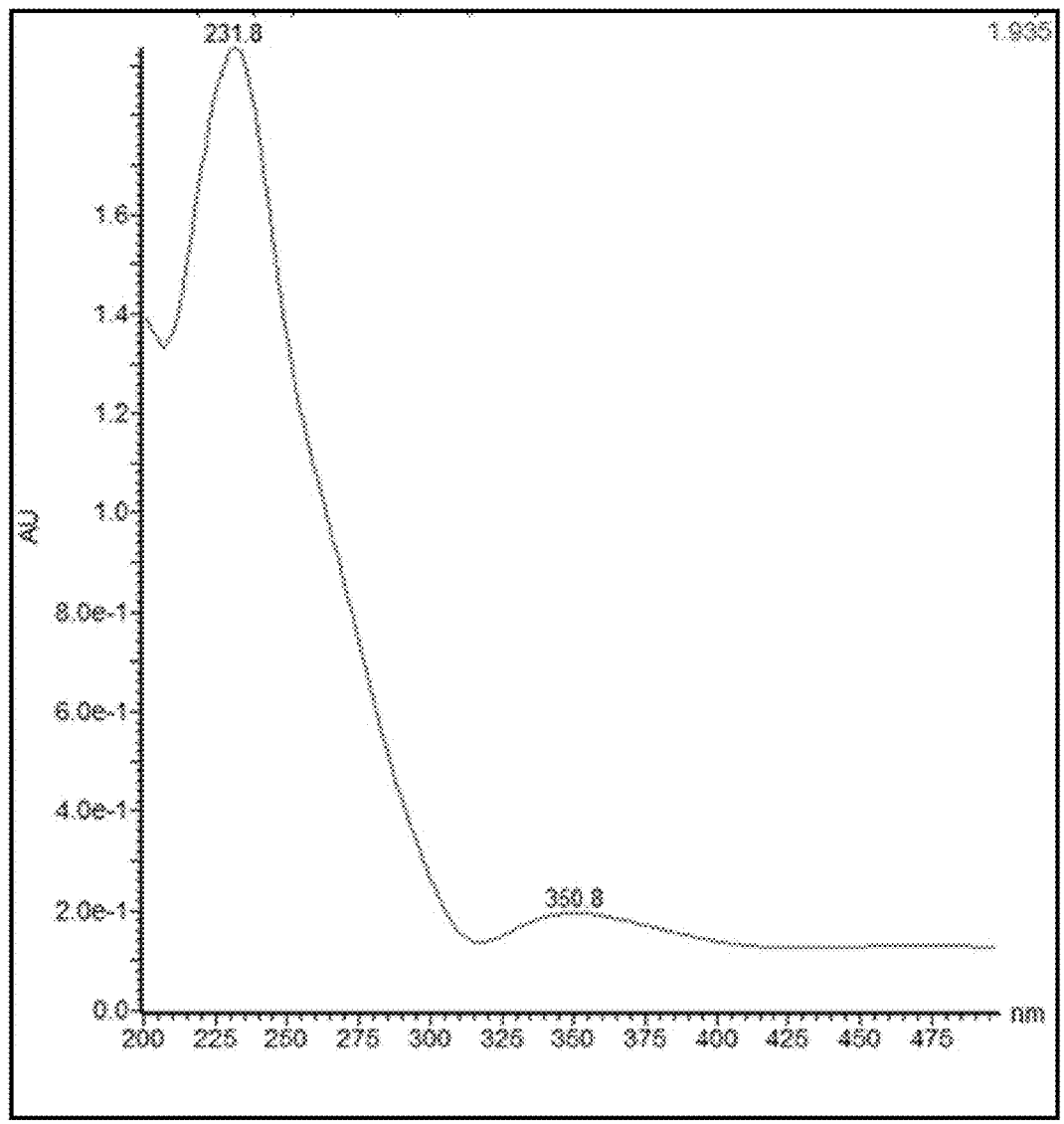

The determination of the exact mass of the dimer (MH+: 631.2428) ($C_{38}H_{35}N_2O_7$) was carried out on an LCT Premier time-of-flight mass spectrometer (Waters). The UV spectrum of the dimeric compound was extracted from the chromatogram obtained on an Acquity system (Waters) equipped with a diode-array UV detector (Acquity PDA detector) (FIG. 4C).

Example 6

In Ovo Study of the Effect of Compound (1) on Tumor Angiogenesis

The effect of compound (1) on tumor angiogenesis was evaluated using the in ovo model based on human tumor grafted onto chick embryo chorioallantoic membrane (CAM).

This experimental approach makes it possible in only a few days to evaluate the tumor's progression and level of vascularization.

Figures 5A, 5B:
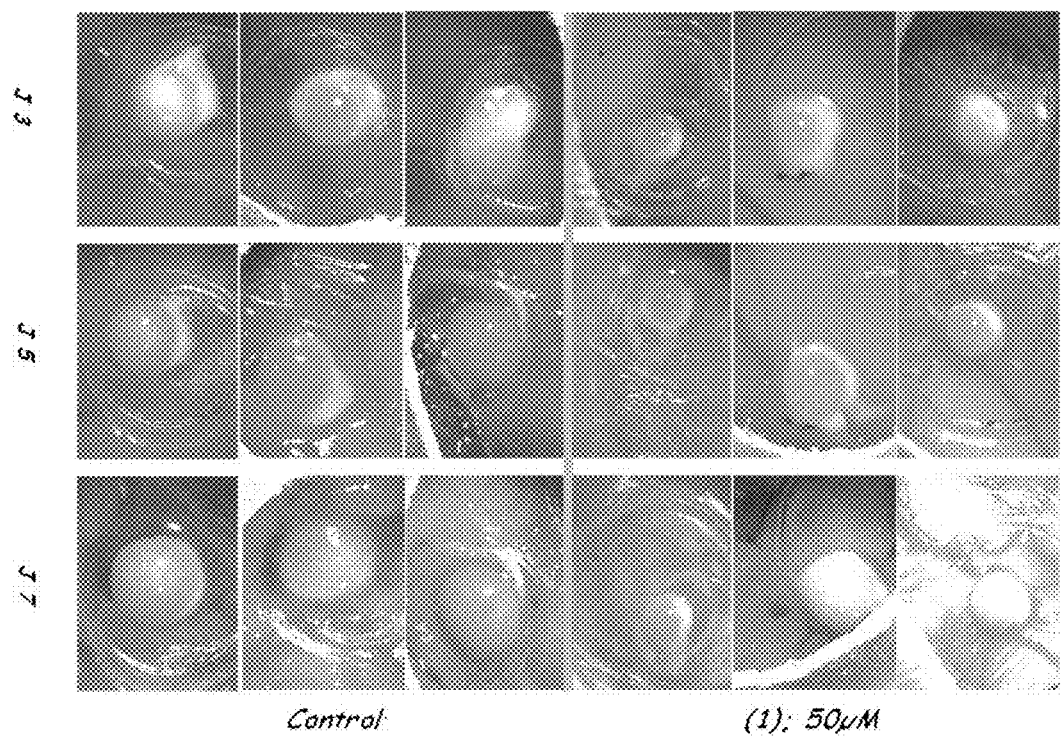
FIG. 5. (A) Inhibitory effect of compound (1) on tumor angiogenesis (human glioblastoma grafted onto the chick embryo chorioallantoic membrane). (B) Study of the dose-dependent effect of compound (1) on VEGF secretion by U87 and HCT-116 cells under normoxic and hypoxic conditions (2% $O_2$).

At the tenth day of embryonic development, glioblastoma cells (U87, $5 \times 10^6$ in 20 µL) were deposited on the chorioallantoic membrane. Two days after the graft, compound (1) at a concentration of 50 µM in a volume of 20 µL was deposited on the surface of the tumor formed. This treatment was repeated every 24 hours for 5 days. The control group was treated with solvent. The test was carried out on 20 eggs bearing glioblastoma tumors for each group. Images of the tumors were taken at day 3 (24 hours after treatment), at day 5 (3 days after treatment) and at day 7 (5 days after treatment) of tumor development. The results presented in FIG. 5A show an inhibition of tumor vascularization after 3 successive treatments (day 5), compared with the control group. This decrease in tumor vascularization also observed at day 7 of tumor development is associated with a significant inhibition of the growth of the treated tumor. These results show a peritumoral antiangiogenic and antitumor activity of compound (1). In order to determine the antiangiogenic mechanism of compound (1), VEGF was assayed by the ELISA method (Invitrogen, Novex technology), from the culture supernatant of U87 and HCT-116 cells, under normoxic and hypoxic conditions. The results indicate (FIG. 5B) that compound (1), at concentrations of 5 to 50 does not modify VEGF secretion after 24 hours of treatment of the cells. These results suggest that the mechanism of peritumoral angiogenesis inhibition of compound (1) may be direct action on endothelial cells.

Example 7

In Ovo Study of the Effect of Compound (1) on Physiological Angiogenesis, on Vasculature Already Formed The effect of compound (1) on physiological angiogenesis was evaluated using the chick embryo chorioallantoic membrane (CAM) model which constitutes a richly vascularized tissue.

Figure 6A:
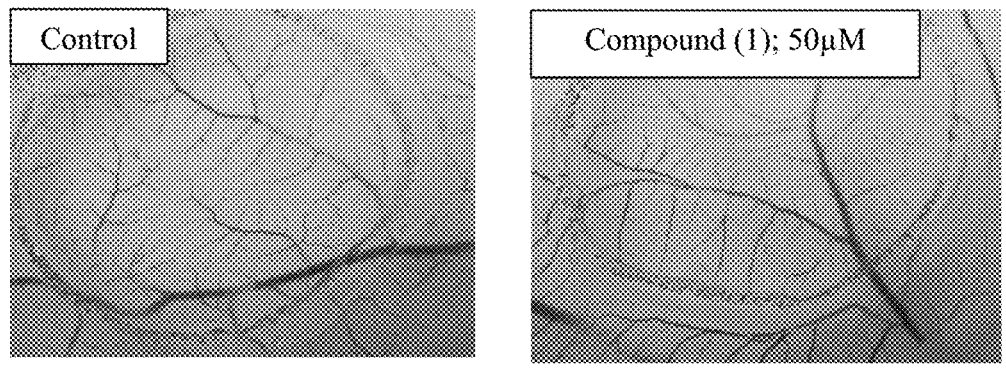
FIG. 6. (A) Absence of the effect of compound (1) on physiological angiogenesis studied in ovo on the chick embryo chorioallantoic membrane model. (B) Effect of compound (1) on the formation of vascular tubes, starting with endothelial cells cultured on Matrigel. (C) Effect of compound (1) on the survival of endothelial cells (HUVEC) cultured in proliferative or quiescent phase for 48 hours.

At the seventh day of embryonic development, 20 µL of the 50 µM solution of compound (1) was deposited on the chorioallantoic membrane whereas the control membranes were treated with solvent. The results presented in FIG. 6A show the absence of the effect of compound (1) on physiological angiogenesis, compared with the control group. These results suggest that compound (1) does not seem to act as an antivascular drug, not modifying the vasculature already formed.

Example 8

Figure 6B:
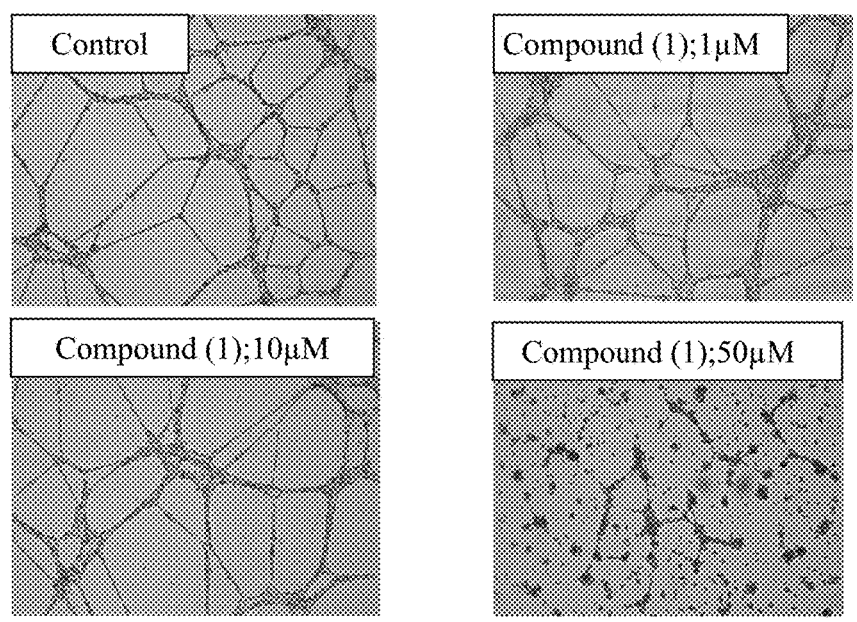

In Vitro Study of the Effect of Compound (1) on "de novo" Formation of Vascular Tubes In order to monitor the effect of compound (1) on "de novo" formation of vascular tubes, human endothelial cells (HUVEC) were cultured in a matrix (Matrigel), in the presence or absence of compound (1). After 24 hours, the effect of compound (1) is analyzed by optical microscopy and is illustrated by photographs. The results (FIG. 6B) show that compound (1) prevents the formation of capillaries (tubes formed from endothelial cells). Compound (1) thus acts directly on growing endothelial cells by blocking the formation of capillaries, in contrast to the absence of effect on a capillary network already formed, in the "quiescent" state.

Example 9

Figure 6C:
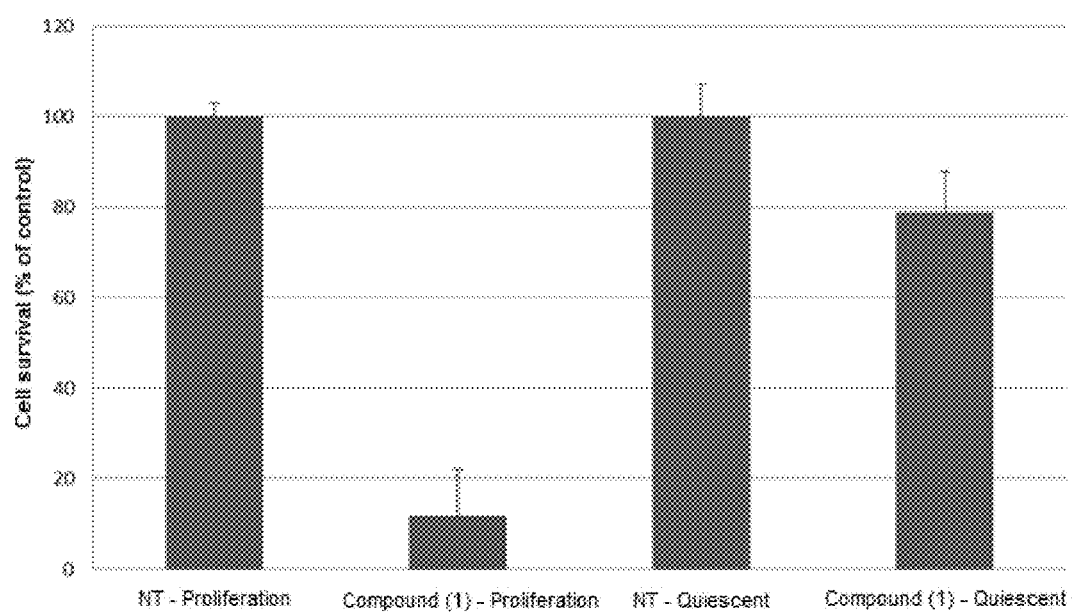

In Vitro Study of the Effect of Compound (1) on Quiescent or Growing Endothelial Cells In order to understand the difference in the observed effects of compound (1) according to whether the vasculature is already formed or is growing "de novo", vascular endothelial cells were cultured at two different cell densities so as to obtain proliferative phase cells or quiescent cells, then treated or not by compound (1), at 10 µM ($IC_{50}$ value: 8 µM) for 48 hours. The results of FIG. 6C show that compound (1) acts only on endothelial cells in the proliferative phase (78% inhibition). This result thus makes it possible to define a specificity of action of compound (1) with respect to endothelial cells in intensive proliferation phase as during peritumoral angiogenesis, the "de novo" formation of vascular tubes or the proliferation of endothelial cells in culture. Compound (1) may thus be used to treat diseases associated with excessive and abnormal angiogenesis, like cancer or ARMD.

Example 10

In Vitro Biological Study on Cancer Cells

The biological activity of compound (1), as well as that of its structural analogues, was studied in vitro on 7 different cancer cell lines:

HCT-116 (colorectal cancer)
U87 (glioblastoma)
K562 (myeloid leukemia) and K562 R
MDA-MB 231 (mammary adenocarcinoma)
MCF-7 (mammary adenocarcinoma)
A549 (pulmonary alveolar adenocarcinoma)

The cells selected for this study were incubated at 37° C. in the presence of compound (1) added in the culture medium at various concentrations and at various times. The set of experiments carried out made it possible to determine the degree of cytotoxicity of the compound tested ($IC_{50}$), its capacity to induce cell death by apoptosis, in close dependence on extracellular superoxide anion for its activation.

1. Study of the Effect of Compound (1) on Cell Growth

The effect of compound (1) on the growth of HCT-116, U87, K562, K562R, MDA-MB 231, MCF-7 and A549 cells, cultured in normoxia, was evaluated using a cell growth test (CellTiter-Blue™ Cell Viability Assay, Promega).

Figure 7B:
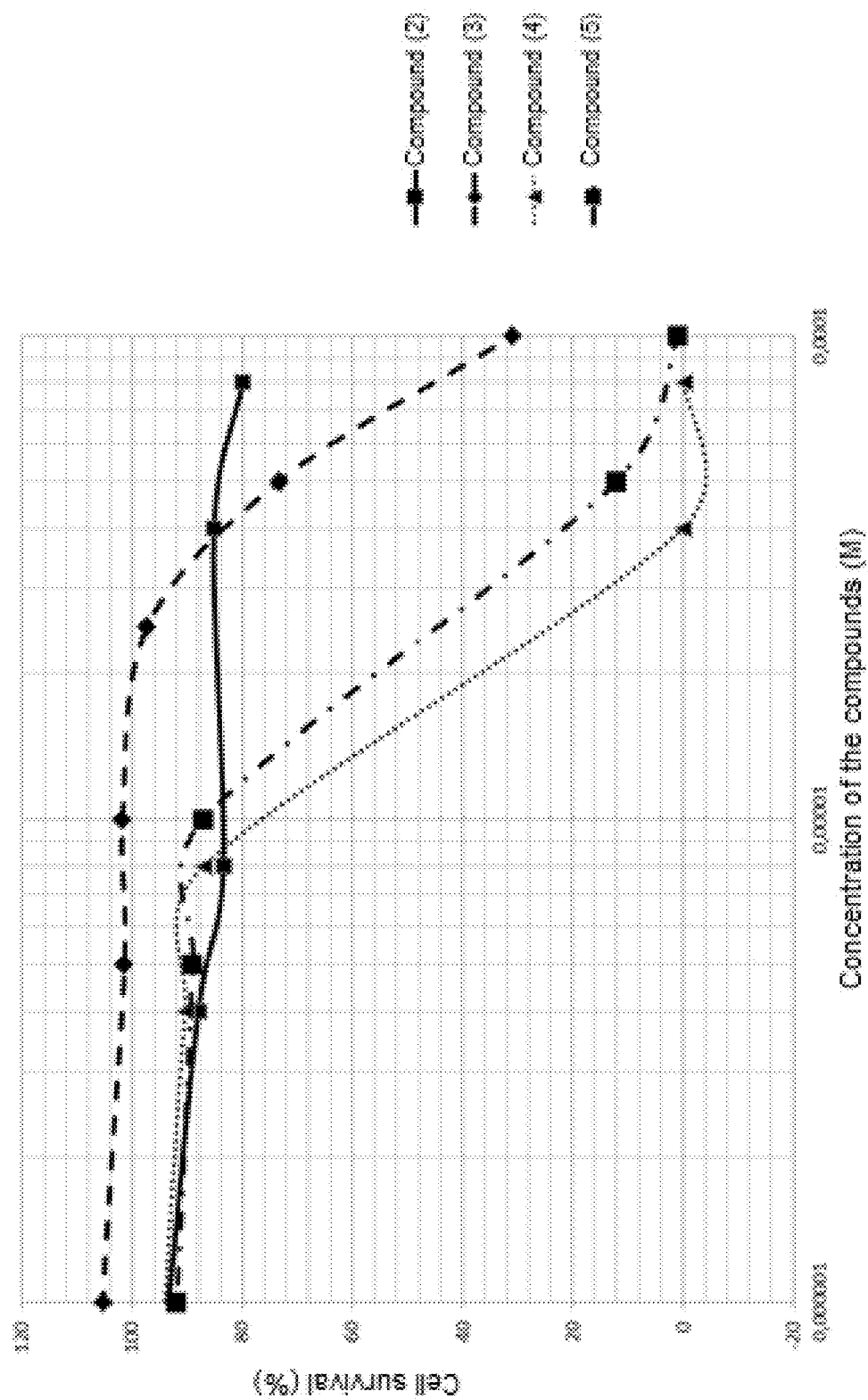
FIG. 7. Evaluation of the biological activity of compound (1) in normoxia. (A) Effect of compound (1) on the growth and cytotoxicity ($IC_{50}$) of HCT 116, U87, MDA-MB-231, A549, MCF-7, K562 and K562 R cancer cells after 72 hours of treatment, (B) Effect of compounds (2), (3), (4), and (5) on the growth of HCT-116 cells after 72 hours of treatment, in normoxia.

The results presented in FIG. 7A show the $IC_{50}$ values (concentration of the compound which induces a 50% decrease in cell growth) determined after 72 hours of treatment with compound (1). It is 7.5 µM for the HCT-116 cells, 7 µM for the U87, 20 µM for the MDA-MB, 231.6 µM for the K562, 12.5 µM for the K562R, 15 µM for the MCF-7 and 15 µM for the A549. The results, presented in FIG. 7B, show the dose-dependent cytotoxic effect of compounds (2), (3), (4) and (5) on HCT-116 cells cultured in normoxia for 72 hours. The absence of catechol leads to the loss of cytotoxicity of compounds (2) and (3), whereas modification of the side chain by a butyl (5) or o-ethoxy (4) chain does not substantially change the $IC_{50}$ value.

Figure 8A:
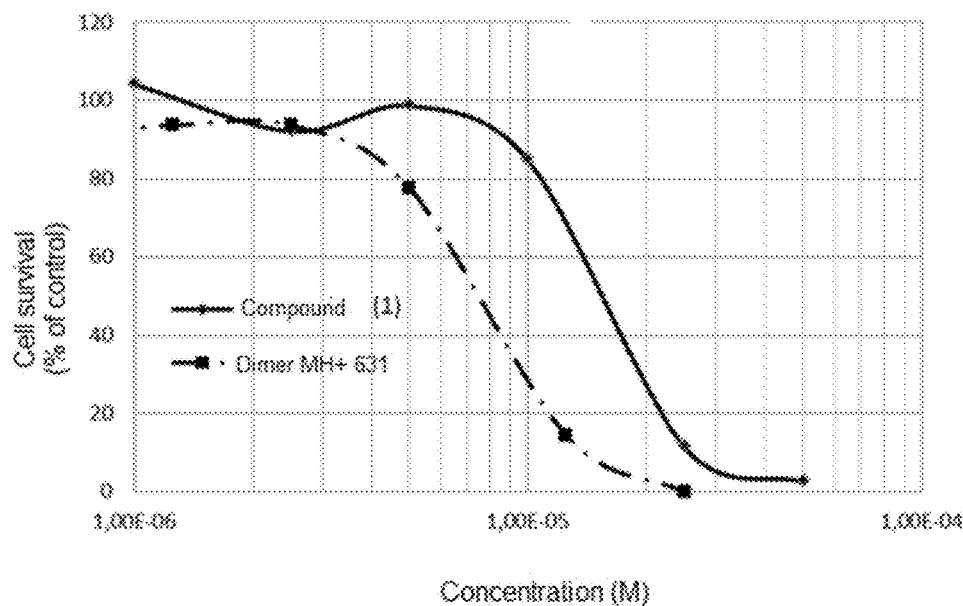
FIG. 8. Effects of compound (1) and of the dimeric compound MH+=631 on the growth ($IC_{50}$) of HCT-116 cancer cells after 48 hours of treatment in normoxia (A) and in hypoxia (B).
Figure 8B:
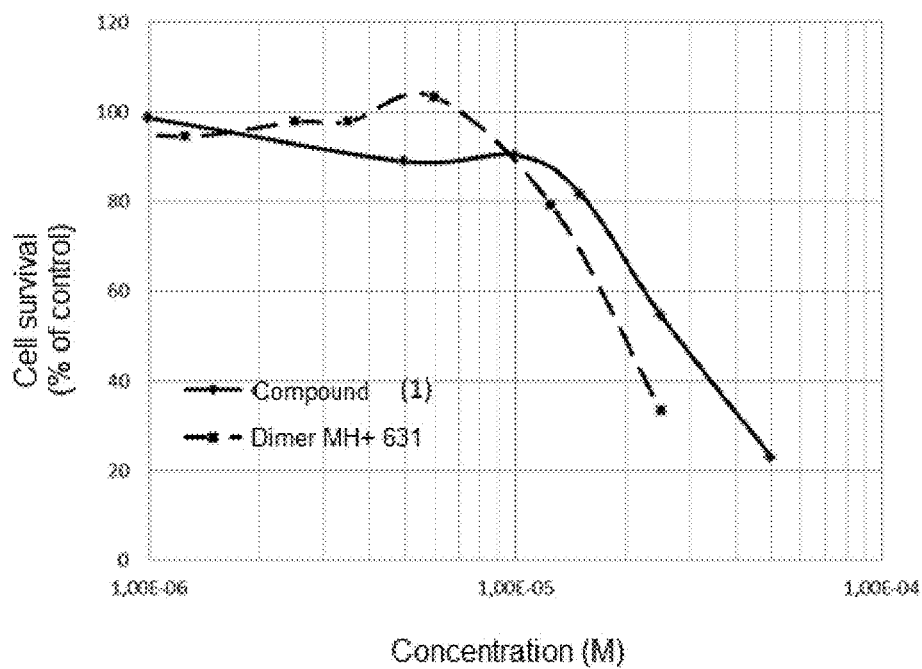

The results, presented in FIG. 8A, show the comparative cytotoxic effect of compound (1) and the dimer MH+ 631 previously obtained by oxidative coupling of compound (1) on HCT-116 cells cultured in normoxia, for 48 hours. The dimer is toxic, with an $IC_{50}$ of 7.5 µM, half that of compound (1), due to the twofold molecular weight of the dimer (MW=630 d). The results, presented in FIG. 8B, show the comparative cytotoxic effect of compound (1) and the dimer MH+631 on HCT-116 cells cultured in hypoxia (2% $O_2$) for 48 hours. The dimer is toxic, with an $IC_{50}$ of 10 µM, approximately half that of compound (1), due to the twofold molecular weight of the dimer.

Figure 9:
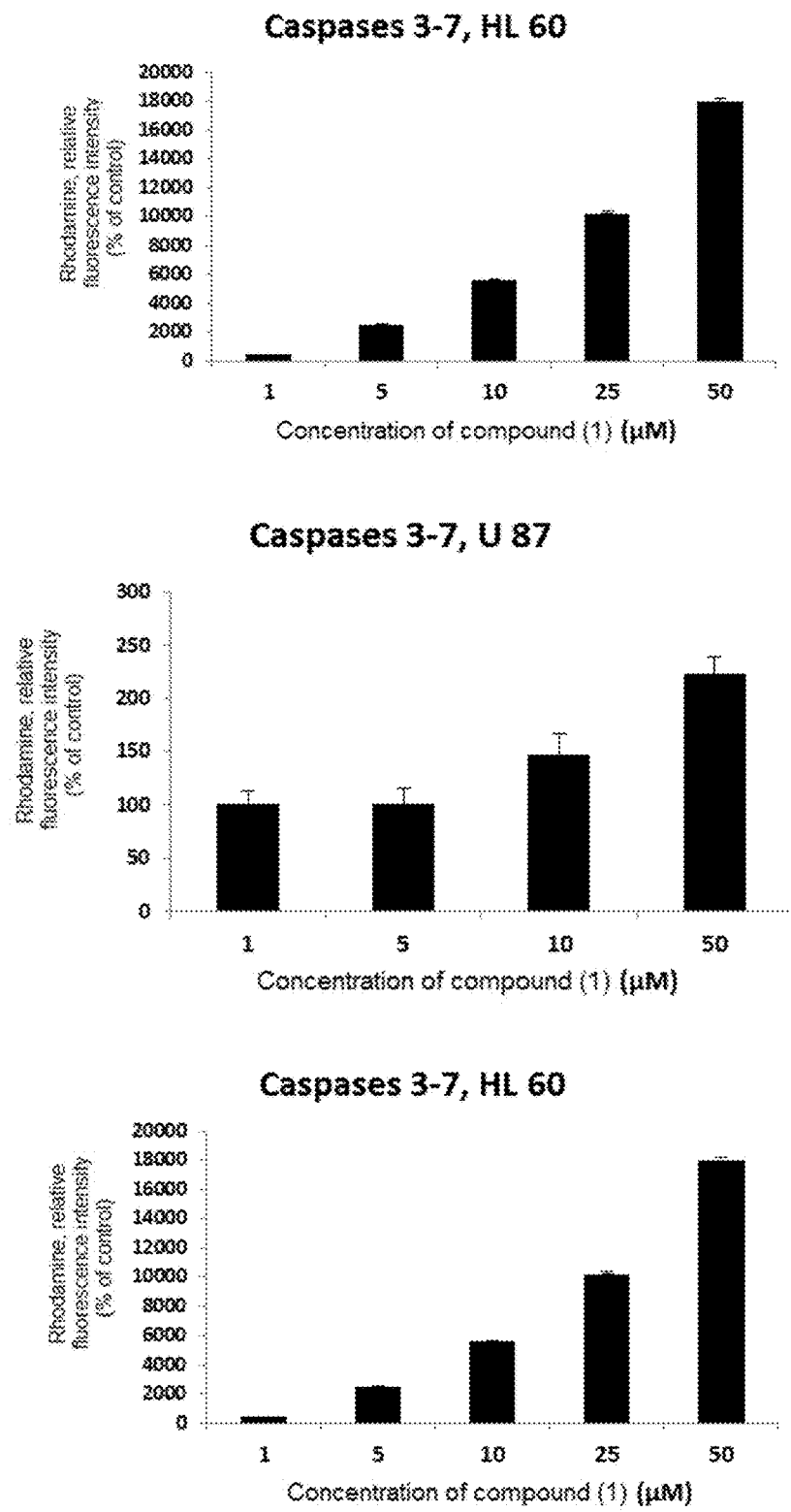
FIG. 9. Effect of compound (1) on the activity of caspases 3 and 7 evaluated on HCT-116, U87 and HL60 cancer cells in normoxia.

2. Study of the Effect of Compound (1) on the Induction of Apoptosis in Normoxia In order to specify whether compound (1) leads to apoptotic cell death, the activity of caspases 3 and 7, marker enzymes of apoptosis, was measured using the ApoONE test (Promega) in HCT-116, U87 and HL60 cells treated in normoxia for 24 hours with compound (1) at concentrations varying from 1 µM to 50 µM. The results, presented in FIG. 9, show that the treatment of cells with compound (1) induces a significant activation of both caspases, irrespective of the cell line. The strongest activation was obtained with HL60 cells.

3. Suppression of the Cellular Superoxide Anion Signal by Compound (1)

Figure 10:
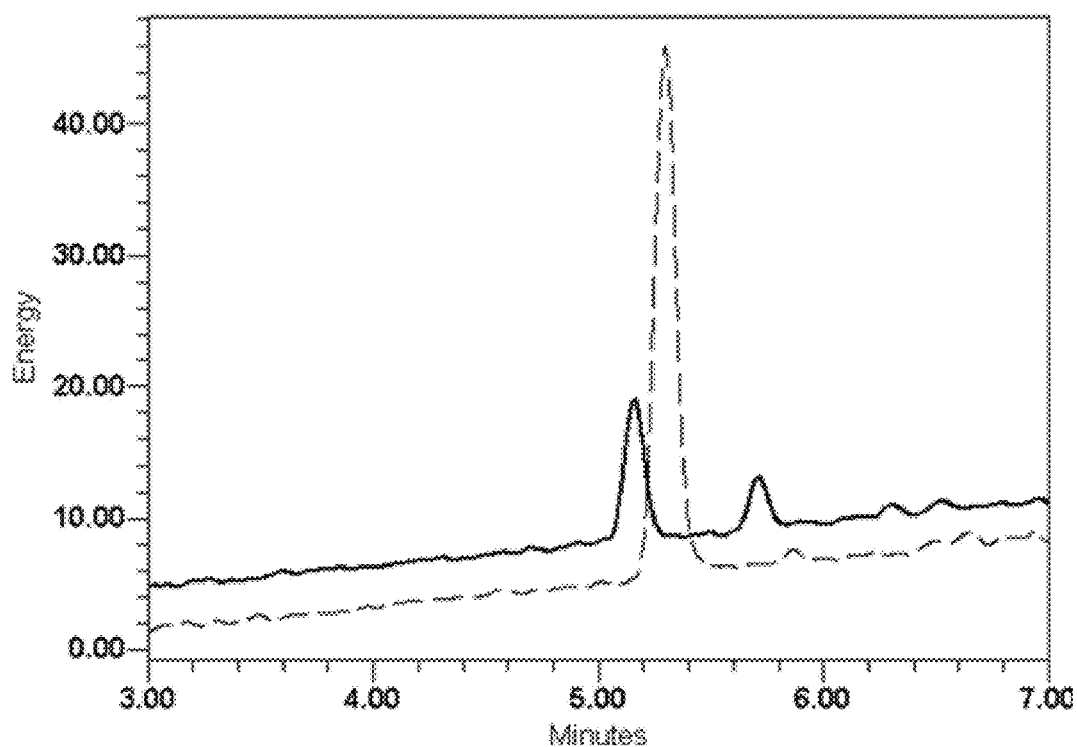
FIG. 10. Suppression of the cellular superoxide anion signal of HCT-116 cells by compound (1) in normoxia. Analysis by HPLC-fluorimetry in the presence of the probe dihydroethidium (DHE). Continuous line: control; dashed line: treated with compound (1).

The effect of compound (1) on superoxide anion was studied following the treatment of HCT-116 cells with 50 µM compound (1) for 3 hours and followed by incubation with the probe dihydroethidium (DHE) (10 µM) for 20 minutes. After removing the culture medium and washing with ice-cold DPBS, the cells were collected in 1 ml of cold DPBS. After centrifugation at 1000 g for 5 minutes, the pellet was taken up in 150 µl of PBS with Triton X100 (0.1%), shaken and centrifuged at 1000 g for 5 minutes. The supernatant was mixed with a 0.2 M solution of $HClO_4$ in methanol, shaken and placed on ice for 2 hours. After centrifugation at 20000 g for 30 minutes, the supernatant is analyzed by HPLC coupled with fluorescence ($\lambda_{ex}$=510 nm, $\lambda_{em}$=595 nm). In the untreated cells (continuous line), the first peak at $t_R$=5.16 minutes corresponds to the oxidized form "E+", product of oxidation by peroxidases, and the second peak at $t_R$=5.71 minutes to the oxidized form 2-OH E+, specific to the interaction with superoxide anion. In the treated cells, the first peak at $t_R$=5.29 minutes corresponding to the oxidized form "E+" is increased, whereas the second peak at $t_R$=5.71 minutes, corresponding to the oxidized form 2OH E+, specific to the interaction with superoxide anion, was suppressed. The results obtained show an inhibition of the 2OH E+ signal corresponding to the oxidized form of DHE by superoxide anion, and an increase in the E+ signal corresponding to oxidation of DHE by peroxidases or catalase, activated by $H_2O_2$. (FIG. 10).

Figure 11A:
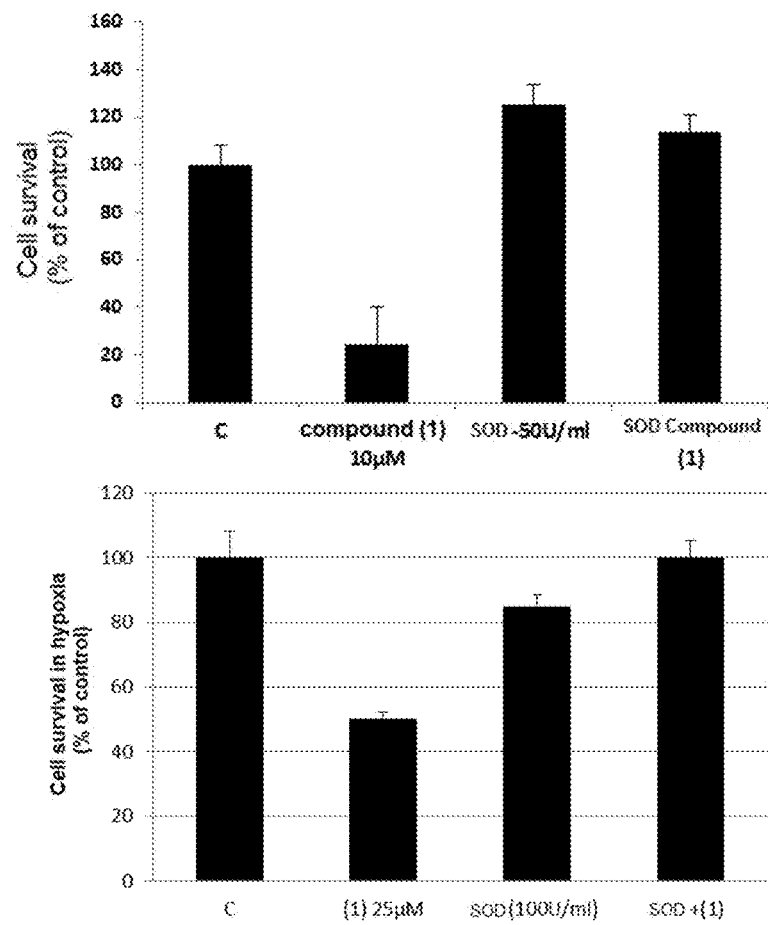
FIG. 11. Dependence of compound (1) on extracellular/membrane superoxide anion for the cytotoxic effects in normoxia and hypoxia (A); for the proapoptotic effects in normoxia: chromatin condensation (B) and caspase 3-7 activity (C): effect of 50 U/ml SOD.
Figure 11B:
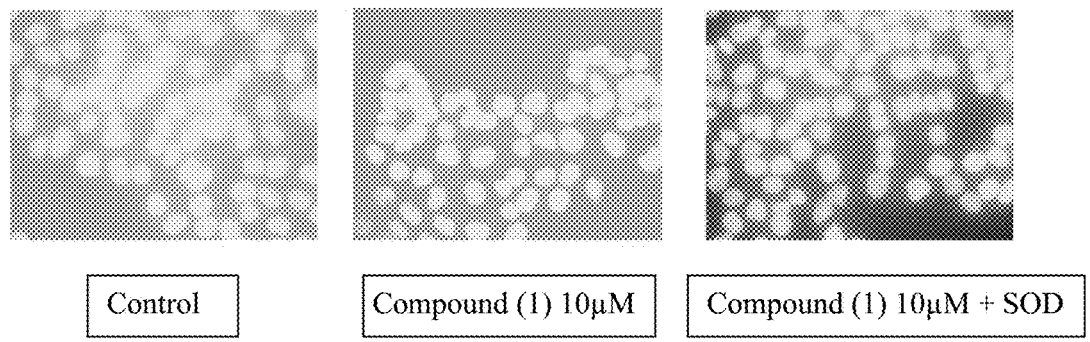
Figure 11C:
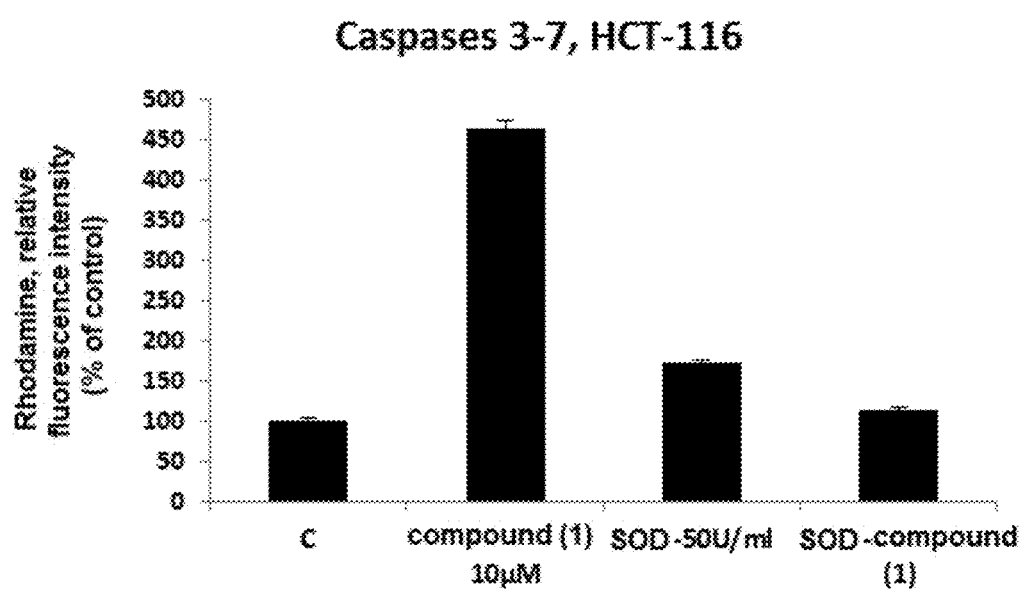

4. Dependence of Compound (1) on Extracellular/Membrane Superoxide Anion for Cytotoxic and Proapoptotic Action In order to determine the role of superoxide anion, produced by the cells, in the activation of compound (1), HCT-116 cells were pretreated for 1 hour with the enzyme superoxide dismutase (SOD1) at 50 U/ml, then treated with compound (1). The cells were analyzed to evaluate, firstly, cell survival in normoxia (72 hours of treatment) and in hypoxia (48 hours of treatment). Secondly, the formation of condensed chromatin in normoxia and the activity of caspases 3 and 7 in normoxia were evaluated. The results, presented in FIG. 11A, show that the suppression of superoxide anion following treatment with SOD completely blocks the cytotoxic effect of compound (1) at 10 µM in normoxia and at 25 µM in hypoxia. Likewise, pretreatment with SOD completely suppresses the increase in condensed chromatin in normoxia visualized after staining with Hoechst 33258 (FIG. 11B). Similarly, the action of compound (1) on the activation of caspases 3-7 in normoxia is completely suppressed by the action of SOD (FIG. 11C). These results suggest that compound (1) is a prodrug specifically activatable by superoxide anion.

The invention claimed is:

1. A compound of formula (I):

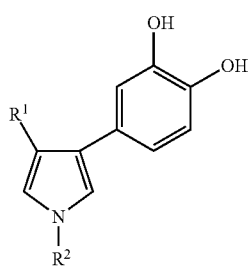

wherein:
R$^1$ represents an aryl group, optionally substituted by one or more ($C_1$-$C_2$)alkyl groups, one or more halogens, one or more —OH, —CN or $CF_3$ groups, and a combination thereof; and
R$^2$ represents a ($C_1$-$C_6$)alkyl group or a hydroxy($C_1$-$C_6$) alkyl group or a ($C_1$-$C_4$)alkoxy($C_1$-$C_6$)alkyl group;
or a pharmaceutically acceptable hydrate or solvate thereof.

2. A compound according to claim 1, characterized in that $R^1$ represents a phenyl and $R^2$ represents a $(C_1-C_6)$alkyl group or a hydroxy$(C_1-C_6)$alkyl group or a $(C_1-C_4)$alkoxy $(C_1-C_6)$alkyl group.

3. A compound according to claim 1, selected from the compounds of the following formulae (Ia), (Ib) and (Ic):

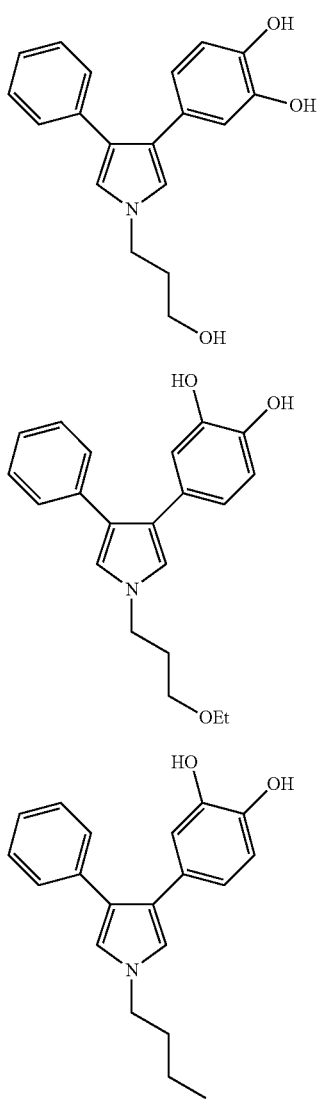

and the pharmaceutically acceptable hydrates and solvates thereof.

4. A compound according to claim 1, for use as a drug for treating colorectal cancer, lung cancer, brain cancer, and leukemia.

5. A compound for use according to claim 4, for use as a prodrug for treating colorectal cancer, lung cancer, breast cancer, brain cancer, and leukemia.

6. A compound for use according to claim 5, characterized in that said prodrug is activated by dimerization.

7. A compound for use according to claim 6, characterized in that said prodrug is activated by dimerization by oxidative coupling.

8. A compound according to claim 6, characterized in that the dimerization is carried out in the presence of superoxide anion.

9. A compound for use according to claim 6, characterized in that the dimerization leads to a compound of general formula (II):

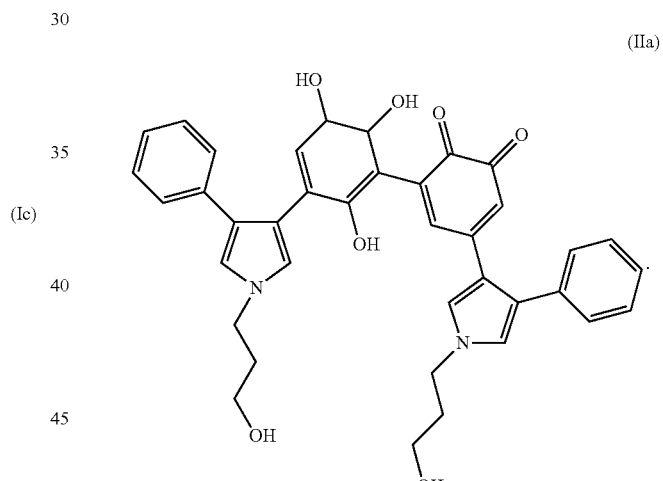

wherein $R^1$ and $R^2$ are as defined in claim 1.

10. A compound for use according to claim 9, characterized in that the dimerization leads to a compound of formula (IIa):

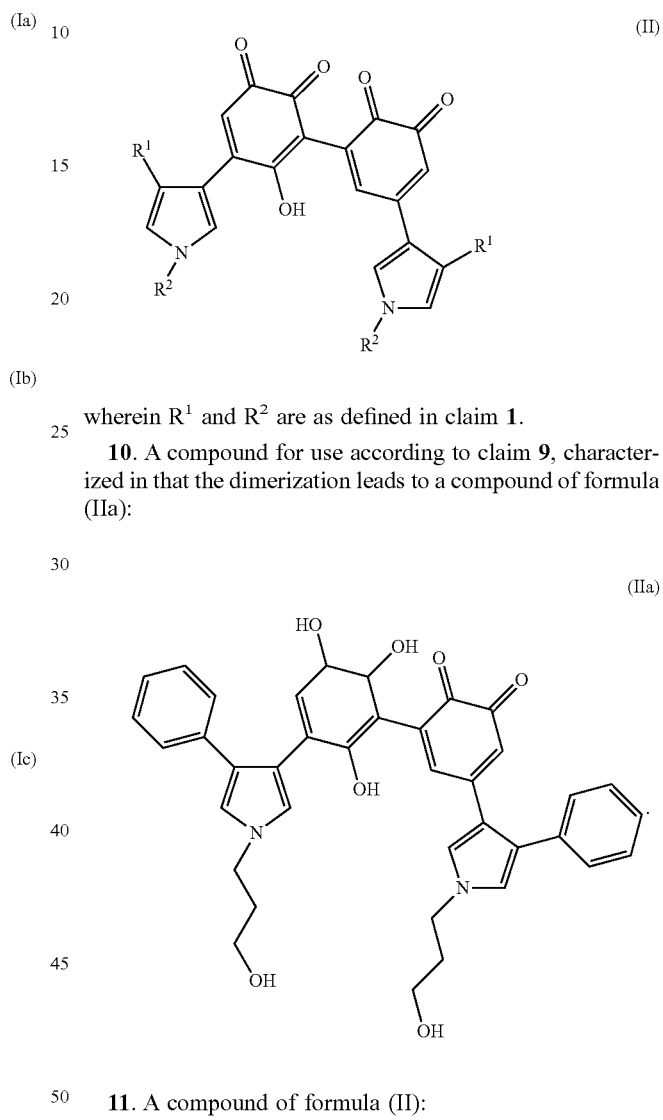

11. A compound of formula (II):

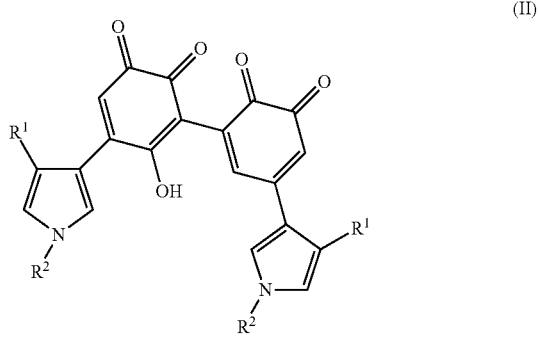

wherein:

R¹ represents an aryl group, optionally substituted by one or more $(C_1-C_2)$alkyl groups, one or more halogens, one or more —OH, —CN or $CF_3$ groups, and a combination thereof.

R² represents a $(C_1-C_6)$alkyl group or a hydroxy$(C_1-C_6)$alkyl group or a $(C_1-C_4)$alkoxy$(C_1-C_6)$alkyl group;

or a pharmaceutically acceptable hydrate or solvate thereof.

12. A compound according to claim 11, for use as a drug for treating colorectal cancer, lung cancer, breast cancer, brain cancer, and leukemia.

13. A compound according to claim 1 or claim 11, for use for treating colorectal cancer, lung cancer, breast cancer, brain cancer, and leukemia.

14. A pharmaceutical composition comprising as a prodrug at least one compound of formula (I) or (II) according to claim 1 or claim 11 and a pharmaceutically acceptable excipient.

15. A pharmaceutical composition comprising as a prodrug at least one compound of formula (I) or (II) according to claim 1 or claim 11 and a pharmaceutically acceptable excipient, for use for treating colorectal cancer, lung cancer, breast cancer, brain cancer, and leukemia.

16. A method for preparing a compound according to claim 1, comprising the condensation reaction of a compound of formula (V):

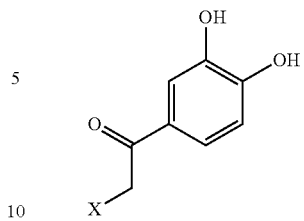
(V)

wherein X is a halogen,
with a compound of the following formula (VI) and a compound of the following formula (VII):

$$R^2—NH_2 \quad (VI)$$

$$R^1—CH_2—CHO \quad (VII)$$

wherein R¹ and R² are as defined in claim 1.

17. A compound according to claim 1, wherein R¹ is phenyl.

18. A compound according to claim 11, wherein R¹ is phenyl.

19. A method according to claim 16, wherein X is a chlorine atom.

* * * * *